(12) United States Patent
Anderskewitz et al.

(10) Patent No.: US 6,365,584 B1
(45) Date of Patent: Apr. 2, 2002

(54) ARYLSULPHONAMIDE-SUBSTITUTED BENZIMIDAZOLES HAVING TRYPTASE-INHIBITING ACTIVITY

(75) Inventors: Ralf Anderskewitz, Bingen (DE); Christine Braun, Guibiasco (CH); Hans Briem, Ingelheim (DE); Bernd Disse, Mainz (DE); Christoph Hoenke, Ingelheim (DE); Hans Michael Jennewein, Wiesbaden (DE); Georg Speck, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/666,765

(22) Filed: Sep. 21, 2000

Related U.S. Application Data
(60) Provisional application No. 60/157,278, filed on Oct. 1, 1999.

(30) Foreign Application Priority Data

Sep. 24, 1999 (DE) .......................... 199 45 787

(51) Int. Cl.[7] ............... A61K 31/55; A61K 31/4725; A61K 31/4184; C07D 401/12; C07D 403/12; A61P 29/00
(52) U.S. Cl. ............ 514/217.09; 514/218; 514/254.08; 514/307; 514/314; 514/322; 514/338; 514/394; 514/415; 514/336; 540/575; 540/603; 544/139; 544/370; 546/145; 546/172; 546/199; 546/273.4; 546/268.4; 548/309.7; 548/310.1; 548/465; 548/503; 548/509
(58) Field of Search ............. 548/309.7; 546/145, 546/172, 199, 273.4; 544/139, 370; 540/575, 603; 514/394, 307, 314, 322, 217.09, 254.08, 218, 338

(56) References Cited

U.S. PATENT DOCUMENTS

| 6,087,380 A | 7/2000 | Hauel et al. |
| 6,121,308 A | 9/2000 | Hauel et al. |

FOREIGN PATENT DOCUMENTS

| WO | WO94 27958 | 12/1994 |
| WO | WO98 37075 | 8/1998 |
| WO | WO99 24407 | 5/1999 |
| WO | WO00 08014 | 2/2000 |

OTHER PUBLICATIONS

Stuerzebecher, J. et al; "Inhibition of human mast cell tryptase by benzamidine derivatives", Biological Chemistry Hoppe–Seyler, Bd. 373, Nr. 10, Oct. 1992, 1025–1030.

Caughey, G. H. et al; "Bis(5–amidino–2–benzimidazolyl)methane and related amidines are potent, reversible inhibitors of mast cell tryptase"; Journal of Pharmacology and Experimental Therapeutics, Bd. 264, Nr. 2, 1993, 676–682.

*Primary Examiner*—Evelyn Mei Huang
(74) *Attorney, Agent, or Firm*—Robert P. Raymond; Alan R. Stempel; Mary-Ellen M. Devlin

(57) ABSTRACT

Arylsulphonamide-substituted benzimidazole derivatives of formula (I)

(I)

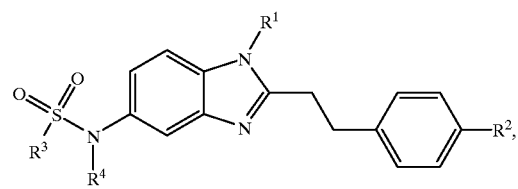

having tryptase-inhibiting activity. Exemplary are:

1-Methyl-2-[2-(4-amidinophenyl)-ethyl]-5-[N-(2-diethylaminoethyl)-benzenesulphonylamino]-benzimidazole;

1-Methyl-2-[2-(4-amidinophenyl)-ethyl]-5-[N-(2-diethlylaminoethyl)-benzylsulfonylamino]-benzimidazole; and, 1-Methyl-2-[2-(4-amidinophenyl)-ethyl]-5-[N-(3-diethylaminopropyl)-benzenesulphonylamino]-benzimidazole.

17 Claims, No Drawings

ARYLSULPHONAMIDE-SUBSTITUTED BENZIMIDAZOLES HAVING TRYPTASE-INHIBITING ACTIVITY

RELATED APPLICATIONS

The benefit of prior provisional application Serial No. 60/157,278, filed on Oct. 1, 1999 is hereby claimed.

FIELD OF THE INVENTION

The invention relates to substituted arylsulphonamide-substituted benzimidazoles having tryptase-inhibiting activity, methods for preparing such compounds and their use for the treatment of inflammatory and/or allergic diseases.

BACKGROUND OF THE INVENTION

Benzimidazole derivatives are known from the prior art as active substances having valuable pharmaceutical properties. Thus, International Patent Application WO 98/37075 discloses, in addition to other bicyclic heterocycles, benzimidazoles which can be used to good effect for the prevention and treatment of venous and arterial thrombotic diseases, on the basis of their thrombin-inhibiting activity.

SUMMARY OF THE INVENTION

In contrast to the use of benzimidazole derivatives as described above and known from the prior art, the aim of the present invention is to prepare new tryptase-inhibitors which can be used, on the basis of their tryptase-inhibiting properties, for the prevention and treatment of inflammatory and/or allergic diseases.

DETAILED DESCRIPTION OF THE INVENTION

The present invention provides new benzimidazoles of general formula (I)

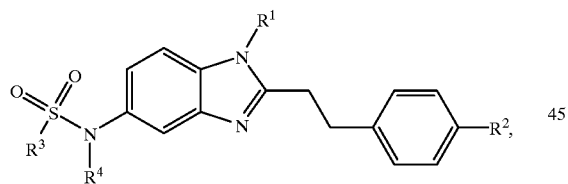

(I)

wherein:
$R^1$ denotes a group selected from the group $C_1$–$C_6$-alkyl, $C_2$–$C_6$-alkenyl and $C_2$–$C_6$-alkinyl, which may optionally be mono-, di- or trisubstituted by one or more of the groups hydroxy, $C_1$–$C_4$-alkoxy, $CF_3$, phenoxy, COOH, halogen, —CO($C_1$–$C_4$-alkoxy), —CONH$_2$, —CO—NH($C_1$–$C_4$-alkyl), —CO—N($C_1$–$C_4$-alkyl)$_2$, —NH$_2$, —NH($C_1$–$C_4$-alkyl), —N($C_1$–$C_4$-alkyl)$_2$ or $C_1$–$C_4$-alkoxy-phenoxy, or a $C_3$–$C_8$-cycloalkyl optionally linked via a $C_1$–$C_4$-alkylene bridge, which may optionally be mono-, di- or trisubstituted by one or more of the groups hydroxy, $C_1$–$C_4$-alkoxy, carboxy, halogen, $C_1$–$C_4$-alkoxycarbonyl or $CF_3$, or phenyl-$C_1$–$C_4$-alkyl, which may optionally be mono-, di- or trisubstituted by one or more of the groups hydroxy, $C_1$–$C_4$-alkoxy, carboxy, halogen, $C_1$–$C_4$-alkoxycarbonyl or $CF_3$, or a 5- or 6-membered, saturated or unsaturated heterocyclic group linked directly or via a $C_1$–$C_4$-alkylene bridge, which may contain one or two hetero atoms selected from the group oxygen, nitrogen or sulphur and which may optionally be substituted by $C_1$–$C_4$-alkyl or benzyl;

$R^2$ denotes —C(=NH)NH$_2$ or —CH$_2$—NH$_2$;

$R^3$ denotes phenyl, benzyl, naphthyl, furanyl, benzofuranyl, quinolyl, isoquinolyl, thienyl or benzothienyl;

$R^4$ denotes hydrogen, a $C_1$–$C_6$-alkyl group, which may be mono- or disubstituted by one or two of the groups —NH$_2$, —NH($C_1$–$C_4$-alkyl), —N($C_1$–$C_4$-alkyl)$_2$, —C(=NH)NH$_2$ or —NH—C(=NH)NH$_2$, or a 5-, 6- or 7-membered, saturated or unsaturated heterocyclic group linked directly or via a $C_1$–$C_4$-alkylene bridge or via a $C_1$–$C_4$-alkylene-CO bridge which may optionally contain one, two or three hetero atoms selected from the group oxygen, nitrogen or sulphur and which may optionally be substituted by $C_1$–$C_4$-alkyl, $C_1$–$C_4$-hydroxyalkyl, benzyl or pyridyl;

$C_3$–$C_8$-cycloalkyl, which may be mono- or disubstituted by one or two of the groups —NH$_2$, —NH($C_1$–$C_4$-alkyl), —N($C_1$–$C_4$-alkyl)$_2$, —C(=NH)NH$_2$ or —NH—C(=NH)NH$_2$, or phenyl, benzyl or phenylethyl, which may be mono- or disubstituted at the phenyl ring by one or two of the groups —NH$_2$, —NH($C_1$–$C_4$-alkyl), —N($C_1$–$C_4$-alkyl)$_2$, —$C_1$–$C_4$-alkyl-NH$_2$, —C(=NH)NH$_2$ or —NH—C(=NH)NH$_2$, optionally in the form of their tautomers, racemates, enantiomers, diastereomers and mixtures thereof, and optionally the pharmacologically acceptable acid addition salts thereof.

According to the invention, the preferred arylsulphonamide-substituted benzimidazole derivatives of general formula (I) are those wherein $R^1$ denotes $C_1$–$C_5$-alkyl, which may optionally be mono-, di- or trisubstituted by one or more of the groups hydroxy, $C_1$–$C_4$-alkoxy, $CF_3$, phenoxy, COOH, —CO($C_1$–$C_4$-alkoxy), —CONH$_2$, —CO—NH($C_1$–$C_4$-alkyl), —CO—N($C_1$–$C_4$-alkyl)$_2$ or $C_1$–$C_4$-alkoxyphenoxy, or a $C_3$–$C_8$-cycloalkyl optionally linked via a $C_1$–$C_4$-alkylene bridge, which may optionally be mono-, di- or trisubstituted by one or more of the groups hydroxy, $C_1$–$C_4$-alkoxy, carboxy, halogen, $C_1$–$C_4$-alkoxycarbonyl or $CF_3$, or phenyl-$C_1$–$C_4$-alkyl, which may optionally be mono-, di- or trisubstituted by one or more of the groups hydroxy, $C_1$–$C_4$-alkoxy, carboxy, $C_1$–C4-alkoxycarbonyl or $CF_3$, or a 5- or 6-membered, saturated or unsaturated heterocyclic group linked directly or via a $C_1$–$C_4$-alkylene bridge, which may contain one or two hetero atoms selected from the group oxygen, nitrogen or sulphur and which may optionally be substituted by $C_1$–$C_4$-alkyl or benzyl;

$R^2$ denotes —C(=NH)NH$_2$ or —CH$_2$—NH$_2$;

$R^3$ denotes phenyl, benzyl, quinolyl, benzothienyl or naphthyl;

$R^4$ denotes a $C_1$–$C_6$-alkyl group, which is mono- or disubstituted by one or two of the groups —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ or —NH—C(=NH)NH$_2$, or a 5-, 6- or 7-membered, saturated or unsaturated nitrogen-heterocyclic group linked directly or via a $C_1$–$C_4$-alkylene bridge or via a $C_1$–$C_4$-alkylene-CO bridge, which may optionally contain one or two other hetero atoms selected from the group oxygen, nitrogen or sulphur and which may optionally be substituted by $C_1$–$C_4$-alkyl, $C_1$–$C_4$-hydroxyalkyl, benzyl or pyridyl;

cyclopropyl, cyclopentyl or cyclohexyl, each of which is mono- or disubstituted by one or two of the groups —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ or —NH—C(=NH)NH$_2$, or phenyl, benzyl or phenylethyl, which are mono- or disubstituted at the phenyl ring by one or two of the groups —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ or —NH—C(=NH)NH$_2$, optionally in the form of their tautomers, racemates, enantiomers, diastereomers and mixtures thereof, and optionally the pharmacologically acceptable acid addition salts thereof.

Preferred are arylsulphonamide-substituted benzimidazole derivatives of general formula (I), wherein $R^1$ denotes methyl, ethyl, propyl, butyl or pentyl, each of which may be substituted by one of the groups hydroxy, methoxy, ethoxy, propoxy, $CF_3$, phenoxy, COOH, $CONH_2$, CONHMe or methoxy-phenoxy, or benzyl, phenylethyl or phenylpropyl, which may be mono- or disubstituted at the phenyl ring by one or two of the groups hydroxy, methoxy, ethoxy, carboxy, methoxycarbonyl, ethoxycarbonyl or $CF_3$, or a 5- or 6-membered, saturated or unsaturated heterocyclic group linked directly or via a $C_1$–$C_4$-alkylene bridge, which may contain one or two hetero atoms selected from the group oxygen or nitrogen and may optionally be substituted by methyl, ethyl, propyl or benzyl;

$R^2$ denotes —C(=NH)NH$_2$ or —CH$_2$—NH$_2$;

$R^3$ denotes phenyl, benzyl, quinolyl, benzothienyl or naphthyl;

$R^4$ denotes a group selected from the group ethyl, propyl, butyl, pentyl and hexyl, each of which is mono- or disubstituted by one or two of the groups —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ or —NH—C(=NH)NH$_2$, or a 5-, 6- or 7-membered, saturated or unsaturated nitrogen-heterocyclic group linked directly or via a $C_1$–$C_4$-alkylene bridge or via a $C_1$–$C_3$-alkylene-CO bridge, which may optionally contain one or two other hetero atoms selected from the group oxygen or nitrogen and may optionally be substituted by methyl, ethyl, propyl, 3-hydroxypropyl or benzyl, or cyclopentyl or cyclohexyl, each of which is mono- or disubstituted by one or two of the groups —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ or —NH—C(=NH)NH$_2$, or benzyl or phenylethyl, which are mono- or disubstituted at the phenyl ring by one or two of the groups —NH$_2$, —NHmethyl, —N(methyl)$_2$, —NHethyl, —N(ethyl)2, —NH(n-propyl), —N(n-propyl)$_2$, —NH(iso-propyl), —N(iso-propyl)$_2$, —C(=NH)NH$_2$ or —NH—C(=NH)NH$_2$, optionally in the form of their tautomers, racemates, enantiomers, diastereomers and mixtures thereof, and optionally the pharmacologically acceptable acid addition salts thereof.

Particularly preferred are arylsulphonamide-substituted benzimidazole derivatives of general formula (I), wherein $R^1$ denotes methyl, ethyl optionally substituted by hydroxy, methoxy, ethoxy, phenoxy or methoxy-phenoxy; propyl optionally substituted by hydroxy, methoxy or ethoxy, or butyl or pentyl, or benzyl which may be mono- or disubstituted at the phenyl ring by one or two of the groups hydroxy, carboxy, methoxycarbonyl, ethoxycarbonyl, methoxy, ethoxy or $CF_3$, phenylethyl or phenylpropyl, or a 5- or 6-membered, saturated or unsaturated heterocyclic group linked directly or via a methylene or ethylene bridge which contains oxygen or nitrogen as the heteroatom and may optionally be substituted by methyl, ethyl, propyl or benzyl;

$R^2$ denotes —C(=NH)NH$_2$ or —CH$_2$—NH$_2$, preferably —C(=NH)NH$_2$;

$R^3$ denotes phenyl, benzyl, quinolyl, benzothienyl or naphthyl, preferably phenyl, quinol-8-yl, benzo[b]thien-3-yl or naphthyl;

$R^4$ denotes ethyl or propyl, each of which is substituted by one of the groups —NH$_2$, —N(methyl)$_2$, —N(ethyl)$_2$, —N(n-propyl)$_2$ or —C(=NH)NH$_2$, or a 5-, 6- or 7-membered, saturated or unsaturated nitrogen-heterocyclic group linked directly or via a methylene or ethylene bridge or a carbonylmethyl bridge, which may contain an oxygen as a further heteroatom and may optionally be substituted by methyl, ethyl, propyl, 3-hydroxypropyl or benzyl, or cyclopentyl or cyclohexyl, each of which is substituted by one of the groups —NH$_2$, —N(methyl)$_2$, —N(ethyl)$_2$, —N(n-propyl)$_2$ or —C(=NH)NH$_2$, or benzyl which is substituted at the phenyl ring by one of the groups —NH$_2$, —N(methyl)$_2$, —N(ethyl)$_2$, —N(n-propyl)$_2$ or —C(=NH)NH$_2$, optionally in the form of their tautomers, racemates, enantiomers, diastereomers and mixtures thereof, and optionally the pharmacologically acceptable acid addition salts thereof.

Also particularly preferred are arylsulphonamide-substituted benzimidazole derivatives of general formula (I), wherein $R^1$ denotes methyl, ethyl, hydroxyethyl, methoxyethyl, methoxy-phenoxy-ethyl, propyl, hydroxypropyl, ethoxypropyl, pentyl, or benzyl, which is mono- or disubstituted at the phenyl ring by one or two of the groups carboxy, ethoxycarbonyl or $CF_3$, phenylethyl or phenylpropyl, or a tetrahydrofuranyl linked via a methylene bridge;

$R^2$ denotes —C(=NH)NH$_2$ or —CH$_2$—NH$_2$, preferably —C(=NH)NH$_2$;

$R^3$ denotes phenyl, benzyl, quinolyl, benzothienyl or naphthyl, preferably phenyl, quinol-8-yl, benzo[b]thien-3-yl or naphthyl;

$R^4$ denotes diethylaminoethyl, diethylaminopropyl, or a pyridine, pyrimidine, pyrrolidine, morpholine, azepine or piperidine linked directly or via a methylene or carbonylmethyl bridge, each of which may be substituted by methyl, 3-hydroxypropyl or benzyl, or cyclohexyl substituted by —N(n-propyl)$_2$, or benzyl which is substituted at the phenyl ring by —N(methyl)$_2$ or —C(=NH)NH$_2$, optionally in the form of their tautomers, racemates, enantiomers, diastereomers and mixtures thereof, and optionally the pharmacologically acceptable acid addition salts thereof.

Of particular importance according to the invention are arylsulphonamide-substituted benzimidazole derivatives of general formula (I), wherein R$^1$ denotes methyl, hydroxyethyl, methoxyethyl, methoxy-phenoxy-ethyl, propyl, hydroxypropyl, ethoxypropyl, phenylethyl, phenylpropyl or a tetrahydrofuranyl linked via a methylene bridge, preferably methyl;

R$^2$ denotes —C(=NH)NH$_2$ or —CH$_2$—NH$_2$, preferably —C(=NH)NH$_2$;

R$^3$ denotes phenyl, benzyl, quinol-8-yl, benzo[b]thien-3-yl or naphthyl;

R$^4$ denotes diethylaminoethyl, diethylaminopropyl, or a pyridine linked directly or via a methylene or ethylene bridge, which may be substituted by methyl or benzyl, or a pyrrolidine linked directly or via a methylene or ethylene bridge, which may be substituted by methyl or benzyl, or a piperidine linked directly or via a methylene or ethylene bridge which may be substituted by methyl or benzyl, or a morpholine linked directly or via a methylene or ethylene bridge, or an azepine linked directly or via a methylene or ethylene bridge, cyclohexyl substituted by —N(n-propyl)$_2$, or benzyl substituted at the phenyl ring by —N(methyl)$_2$, optionally in the form of their tautomers, racemates, enantiomers, diastereomers and mixtures thereof, and optionally the pharmacologically acceptable acid addition salts thereof.

The following compounds are of particular interest according to the invention:

1-Methyl-2-[2-(4-amidinophenyl)-ethyl]-5-[N-(2-diethylaminoethyl)-benzenesulphonylamino]-benzimidazole;

1-Methyl-2-[2-(4-amidinophenyl)-ethyl]-5-[N-(2-diethylaminoethyl)-benzylsulfonylamino]-benzimidazole;

1-Methyl-2-[2-(4-amidinophenyl)-ethyl]-5-[N-(3-diethylaminopropyl)-benzenesulphonylamino]-benzimidazole;

1-Methyl-2-[2-(4-amidinophenyl)-ethyl]-5-{N-[(N'-methyl-pyrrolidin-3-yl)methyl]-benzenesulphonylamino}-benzimidazole;

1-Methyl-2-[2-(4-amidinophenyl)-ethyl]-5-{N-[(N'-methyl-pyrrolidin-2-yl)methyl]-benzenesulphonylamino}-benzimidazole;

1-Methyl-2-[2-(4-amidinophenyl)-ethyl]-5-{N-[(N'-benzyl-pyrrolidin-3-yl)]-benzenesulphonylamino}-benzimidazole;

1-Methyl-2-[2-(4-amidinophenyl)-ethyl]-5-[N-(pyrrolidin-3-yl)-benzenesulphonylamino]-benzimidazole;

1-Methyl-2-[2-(4-amidinophenyl)-ethyl]-5-[N-(piperidin-4-yl)-benzenesulphonylamino]-benzimidazole;

1-Methyl-2-[2-(4-amidinophenyl)-ethyl]-5-[N-(N'-benzyl-piperidin-4-yl)-benzenesulphonylamino]-benzimidazole;

1-(2-Methoxyethyl)-2-[2-(4-amidinophenyl)-ethyl]-5-[N-(2-diethylaminoethyl)-benzenesulphonylamino]-benzimidazole;

1-[2-(2-Methoxyphenoxy)ethyl)-2-[2-(4-amidinophenyl)-ethyl]-5-[N-(2-diethylaminoethyl)-benzenesulphonylamino]-benzimidazole;

1-Methyl-2-[2-(4-amidinophenyl)-ethyl]-5-[N-(2-diethylaminoethyl)-naphth-1-ylsulphonylamino]-benzimidazole;

1-Methyl-2-[2-(4-amidinophenyl)-ethyl]-5-[N-(2-diethylaminoethyl)-naphth-2-ylsulphonylamino]-benzimidazole;

1-Methyl-2-[2-(4-amidinophenyl)-ethyl]-5-[N-(2-azepin-1-ylethyl)-benzenesulphonylamino]-benzimidazole;

1-Methyl-2-[2-(4-amidinophenyl)-ethyl]-5-[N-(2-piperidin-1-ylethyl)-benzenesulphonylamino]-benzimidazole;

1-Methyl-2-[2-(4-amidinophenyl)-ethyl]-5-[N-(2-pyrrolidin-1-ylethyl)-benzenesulphonylamino]-benzimidazole;

1-Methyl-2-[2-(4-amidinophenyl)-ethyl]-5-[N-(2-diethylaminoethyl)-benzo[b]thien-3-ylsulphonylamino]-benzimidazole;

1-Methyl-2-[2-(4-amidinophenyl)-ethyl]-5-[N-(pyrid-2-ylmethyl)-naphth-2-ylsulphonylamino]-benzimidazole;

1-Methyl-2-[2-(4-amidinophenyl)-ethyl]-5-[N-(pyrid-3-ylmethyl)-naphth-2-ylsulphonylamino]-benzimidazole;

1-Methyl-2-[2-(4-amidinophenyl)-ethyl]-5-[N-(4'-benzyl-piperid-1-yl-carbonylmethyl)-naphth-2-ylsulphonylamino]-benzimidazole 1-Methyl-2-[2-(4-amidinophenyl)-ethyl]-5-[N-(2-morpholinoethyl)-naphth-2-ylsulphonylamino]-benzimidazole 1-Methyl-2-[2-(4-amidinophenyl)-ethyl]-5-[N-(piperazin-1-yl-carbonylmethyl)-naphth-2-ylsulphonylamino]-benzimidazole 1-Methyl-2-[2-(4-amidinophenyl)-ethyl]-5-[N-(4'-pyrid-4"-yl-piperazin-1-yl-carbonylmethyl)-naphth-2-ylsulphonylamino]-benzimidazole 1-Methyl-2-[2-(4-amidinophenyl)-ethyl]-5-[N-(4'-benzyl-piperazin-1-yl-carbonylmethyl)-naphth-2-ylsulphonylamino]-benzimidazole 1-Methyl-2-[2-(4-amidinophenyl)-ethyl]-5-[N-(4'-(3"-hydroxypropyl)-piperazin-1 -yl-carbonylmethyl)-naphth-2-ylsulphonylamino]-benzimidazol 1-Methyl-2-[2-(4-amidinophenyl)-ethyl]-5-[N-(2-diethylaminoethyl)-chinol-8-ylsulphonylamino]-benzimidazole;

1-Methyl-2-[2-(4-amidinophenyl)-ethyl]-5-[N-(2-diethylaminoethyl)-isochinol-5-ylsulphonylamino]-benzimidazole;

1-Methyl-2-[2-(4-amidinophenyl)-ethyl]-5-[N-(4-dimethylaminobutyl)-benzenesulphonylamino]-benzimidazole;

1-Methyl-2-[2-(4-amidinophenyl)-ethyl]-5-[N-(4-methyl-1,4-diazepin-1-yl-carbonylmethyl)-benzenesulphonylamino]-benzimidazole.

A further aspect of the present invention is directed to the use of the compounds of general formula (I) for preparing a pharmaceutical composition for the prevention and/or treatment of diseases in which tryptase inhibitors may be of therapeutic value.

It is preferred according to the invention to use compounds of general formula (I) for the purpose mentioned above, for preparing a pharmaceutical composition for the prevention and/or treatment of inflammatory and/or allergic diseases. It is particularly preferable to use the compounds of general formula (I) as mentioned above for preparing a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasm.

In addition to the abovementioned compounds of general formula (I) the present invention also relates to compounds which are only converted into the therapeutically effective compounds of general formula (I) by the body after being taken by the patient, on the basis of a functionality which can be cleaved in vivo. Such compounds are known as prodrugs. According to another aspect the invention therefore relates to prodrugs of general formula (II)

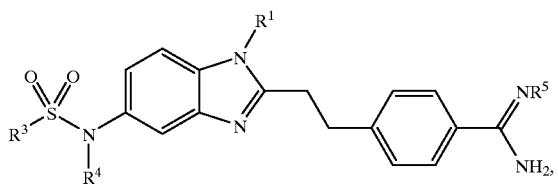

(II)

wherein $R^1$ and $R^3$ may be as hereinbefore defined and $R^4$ may be as hereinbefore defined or may denote $C_1$–$C_4$-alkyl which is substituted by a group selected from the group —C(=NOH)NH2, —C(=NCOO—$C_1$–$C_{12}$-alkyl)NH$_2$ or —C(=NCOO—$C_1$–$C_8$-alkyl-phenyl)NH$_2$;

$R^5$ may denote hydroxy, —COO—$C_1$–$C_{12}$-alkyl, —CO-phenyl, —CO-pyridyl or —COO—$C_1$–$C_8$-alkyl-phenyl, whilst in the abovementioned group the phenyl ring may be substituted in each case by $C_1$–$C_4$-alkyl, $C_1$–$C_4$-alkoxy, OH, halogen or $CF_3$,
optionally in the form of their tautomers, racemates, enantiomers, diastereomers and mixtures thereof, and optionally the pharmacologically acceptable acid addition salts thereof.

Preferred are prodrugs of general formula (II), wherein $R^1$ and $R^3$ may be as hereinbefore defined and $R^4$ may be as hereinbefore defined or may denote $C_1$–$C_4$-alkyl which is substituted by a group selected from among —C(=NOH)NH$_2$, —C(=NCOO—$C_1$–$C_6$-alkyl)NH$_2$ or —C(=NCOO—$C_1$–$C_6$-alkyl-phenyl)NH$_2$;

$R^5$ may denote hydroxy, —COO—$C_1$–$C_6$-alkyl, —CO-phenyl, —CO-pyridyl or —COO—$C_1$–$C_6$-alkyl-phenyl, whilst in the abovementioned group the phenyl ring may be substituted in each case by $C_1$–$C_4$-alkyl, $C_1$–$C_4$-alkoxy, OH, halogen or $CF_3$,
optionally in the form of their tautomers, racemates, enantiomers, diastereomers and mixtures thereof, and optionally the pharmacologically acceptable acid addition salts thereof.

Particularly preferred are prodrugs of general formula (II), wherein $R^1$, $R^3$ and $R^4$ may be as hereinbefore defined and $R^5$ may denote hydroxy, methoxycarbonyl, ethoxycarbonyl, propyloxycarbonyl, butyloxycarbonyl, benzoyl, benzyloxycarbonyl or nicotinoyl,
optionally in the form of their tautomers, racemates, enantiomers, diastereomers and mixtures thereof, and optionally the pharmacologically acceptable acid addition salts thereof.

The term alkyl groups (including those which are part of other groups), unless otherwise stated, denotes branched and unbranched alkyl groups with 1 to 12 carbon atoms, preferably 1–8 carbon atoms, most preferably 1 to 6 carbon atoms. Examples are: methyl, ethyl, propyl, butyl, pentyl, hexyl, etc. Unless otherwise stated, the above terms propyl, butyl, pentyl or hexyl also include all the possible isomeric forms. For example, the term propyl also includes the two isomeric groups n-propyl and iso-propyl, the term butyl includes n-butyl, iso-butyl, sec. butyl and tert.-butyl, the term pentyl includes iso-pentyl, neopentyl, etc. In some cases common abbreviations are also used to denote the abovementioned alkyl groups, such as Me for methyl, Et for ethyl etc.

The term alkenyl groups (including those which are part of other groups) denotes branched and unbranched alkenyl groups having 2 to 6 carbon atoms, preferably 2 to 4 carbon atoms, provided that they have at least one double bond, for example the alkyl groups mentioned above as well, provided that they have at least one double bond, such as for example vinyl (provided that no unstable enamines or enolethers are formed), propenyl, iso-propenyl, butenyl, pentenyl and hexenyl.

The term alkinyl groups (including those which are part of other groups) denotes alkinyl groups having 2 to 6 carbon atoms, provided that they have at least one triple bond, e.g. ethinyl, propargyl, butinyl, pentinyl and hexinyl.

The term halogen generally denotes fluorine, chlorine, bromine or iodine.

Examples of cycloalkyl groups with 3–8 carbon atoms according to the invention are selected from among cyclopropyl, cyclobutyl, cyclopentyl, cyclohexyl, cycloheptyl and cyclooctyl.

Examples of 5-, 6- or 7-membered, saturated or unsaturated heterocycles which may contain nitrogen, oxygen or sulphur as heteroatoms, include, unless otherwise stated in the definitions, furan, tetrahydrofuran, tetrahydrofuranon, γ-butyrolactone, α-pyran, γ-pyran, dioxolan, tetrahydropyran, dioxane, thiophene, dihydrothiophene, thiolan, dithiolan, pyrrole, pyrroline, pyrrolidine, pyrazole, pyrazoline, pyrazolidine, imidazole, imidazoline, imidazolidine, triazole, tetrazole, pyridine, piperidine, pyridazine, pyrimidine, pyrazine, piperazine, triazine, tetrazine, morpholine, thiomorpholine, diazepan, oxazole, isoxazole, oxazine, thiazole, isothiazole, thiadiazole, oxadiazole and pyrazolidine, wherein the heterocyclic group may be substituted as stated in the definitions.

Unless otherwise specified, the two alkyl groups in the dialkylaminosubstituents —N($C_1$–$C_4$-alkyl)$_2$ may be identical or different.

"=O" denotes an oxygen atom linked via a double bond.

The substituted benzimidazole derivatives of formula (I) as well as the prodrugs of general formula (II) may be obtained by various methods of synthesis. Possible approaches based on and using conventional methods of chemical synthesis are hereinafter described by way of example. Diagram 1 shows one possible method of synthesising the basic benzimidazole structure of the compounds according to the invention.

Diagram 1

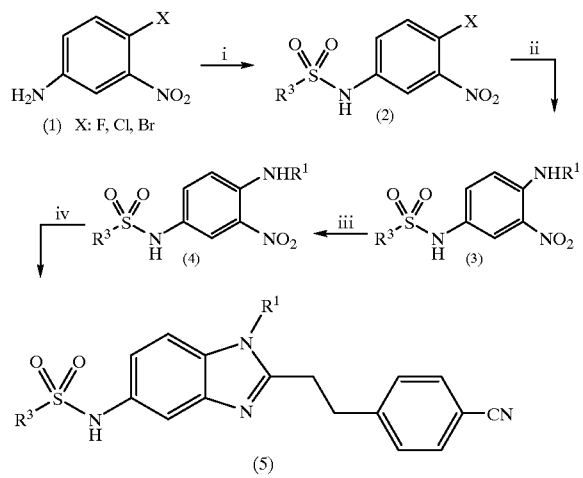

In a first step (diagram, step i) the 3-nitro-4-halo-anilines (1) are reacted to form the sulphonamides (2). For this purpose the compounds (1) are taken up in a suitable organic, anhydrous solvent and combined with the desired arylsulphonic acid chloride optionally in the presence of an organic base, while cooling. Suitable organic solvents may be halogenated hydrocarbons such as dichloromethane or chloroform as well as solvents selected from among dioxan, tetrahydrofuran, dimethylformamide, acetonitrile and pyridine. It is preferred according to the invention to use pyridine or pyridine mixed with dichloromethane or chloroform as solvent. If an organic base is added, amines such as triethylamine, diisopropylethylamine, N-methylmorpholine or pyridine are primarily used. The arylsulphonic acid chloride is preferably added at temperatures below ambient temperature, particularly between −40° C. and 20° C., most preferably at −20° C. to 10° C. After the reaction has ended (about 0.5–2 h) the mixture is worked up by conventional methods. The compounds (2) may optionally be purified by crystallisation from nonpolar organic solvents such as, for example, diethylether and petroleum ether, optionally mixed with ethyl acetate.

In a second step (Diagram 1, step ii) the sulphonamides (2) are reacted to form the compounds (3). The aminolysis of the compounds (2) with the primary amines $R^1$—$NH_2$ is carried out in suitable organic solvents such as for example dimethylsulphoxide, N,N-dimethylformamide, N-methylpyrrolidone, acetone or optionally in water or alcohols at ambient temperature or in a temperature range from 30–80° C., preferably 40–50° C.

The reduction of the nitro groups to form the compounds (4, Diagram 1, step iii) is carried out for example by catalytic hydrogenation in organic solvents such as for example methanol, ethanol, isopropanol, tetrahydrofuran, optionally also in admixture with dimethylformamide, ethyl acetate, dioxan or acetic acid, at elevated hydrogen pressure or at normal pressure at temperatures between 0–50° C., preferably at 20–40° C. Suitable catalysts are conventional hydrogenation catalysts. Palladium and Raney nickel are preferred. According to the invention, palladium is preferred. Palladium on charcoal (5%) is particularly preferred as the catalyst. An alternative method of reducing the nitro compounds (3) envisages the use of reduction agents such as $Na_2S_2O_4$ or $SnCl_2$. This reaction is carried out in protic, water-miscible organic solvents such as short-chained alcohols (methanol, ethanol, isopropanol) or in a mixture of the abovementioned solvents with water, optionally with acetic acid, dimethylformamide or ethyl acetate. The reaction is normally carried out at elevated temperature, preferably by refluxing the solvent or solvent mixture in question. After the reaction of the starting compounds (3) is complete, the mixture is worked up in the usual way. The compounds (4) may be purified for example by crystallisation from nonpolar organic solvents such as diethylether, petroleum ether, optionally mixed with ethyl acetate.

In a fourth step (Diagram 1, step iv) cyclisation to form the benzimidazoles (5) is carried out by reacting the sulphonamide derivatives (4) with p-cyanophenylpropionic acid in the presence of dehydrating reagents. The reaction is optionally carried out in a solvent or mixture of solvents such as methylene chloride, dimethylformamide, benzene, toluene, chlorobenzene, tetrahydrofuran, benzene/tetrahydrofuran or dioxan. Suitable dehydrating agents include for example isobutyl chloroformate, tetraethyl orthocarbonate, trimethyl orthoacetate, 2,2-dimethoxypropane, tetramethoxysilan, phosphorus oxychloride, thionylchloride, trimethylchlorosilan, phosphorus trichloride, phosphorus pentoxide, ethyl 1,2-dihydro-2-ethoxy-quinoline-1-carboxylate (EEDQ), i-propyl 1,2-dihydro-2-i-propyloxy-quinoline-1-carboxylate (IIDQ), N,N'-dicyclohexylcarbodiimide, N,N'-dicyclohexylcarbodiimide/N-hydroxysuccinimide, N,N'-dicyclohexylcar-bodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride. It may be appropriate to add a base such as pyridine, 4-dimethylaminopyridine, N-methyl-morpholine or triethylamine. The reaction is usually carried out at temperatures between 0 and 150° C., preferably at temperatures between 20 and 120° C.

An alternative method of obtaining the compounds (5) is shown by way of example in Diagram 2.

Diagram 2

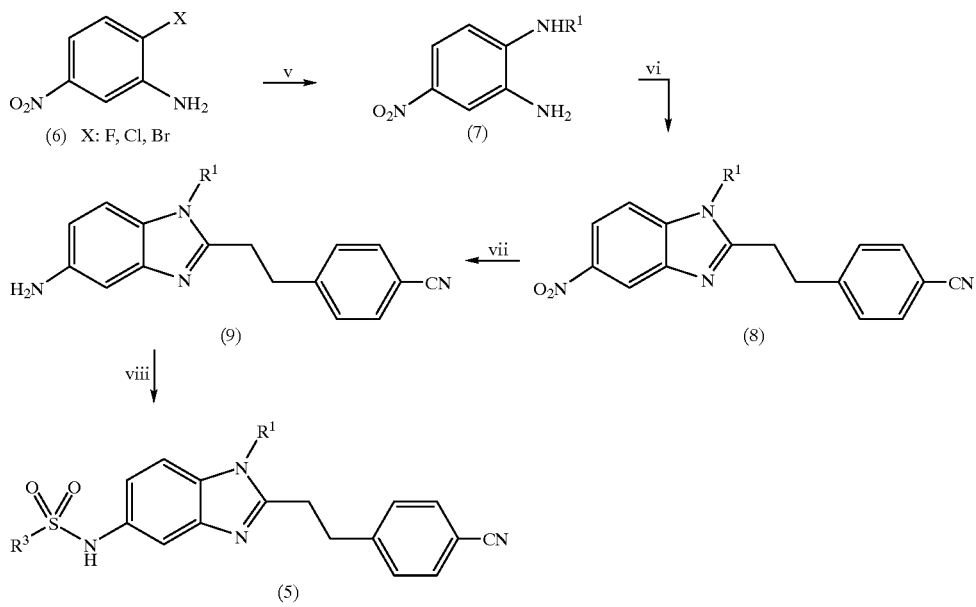

Starting from the 2-halo-5-nitro-anilines (6) aminolysis may first be carried out to obtain the diaminonitrobenzenes (7) according to Diagram 2 (step v). Reacting the compounds (7) with p-cyanophenylpropionic acid leads to the nitro-benzimidazoles (8, step vi), which can be reductively converted into the amino-benzimidazoles (9) (step vii, Diagram 2). The compounds (5) may be obtained from the amino-benzimidazoles (9) by reaction with the corresponding arylsulphonic acid chlorides (Diagram 2, step viii). The synthesis outlined in Diagram 2 may be carried out experimentally analogously to the procedure described for steps i–iv (Diagram 1). Step v is carried out analogously to the method according to step ii, step vi analogously to the method according to step iv, step vii analogously to the method described for step ii and, finally, step viii according to the experimental method in step i.

Starting from the benzimidazoles (5) which may be obtained according to Diagrams 1 and 2, the intermediates of formula (III) (cf. Diagram 3) are obtained by reaction with the compounds $R^4$-Nu, where Nu denotes a nucleofugic leaving group such as for example chlorine, bromine, iodine, methanesulphonate, methyltriflate, p-toluenesulphonate etc. Alternatively, the intermediates (III) may be obtained from the compounds (5) by reductive amination by reacting with correspondingly substituted ketones or aldehydes under reductive conditions.

Schema 3

Diagram 3

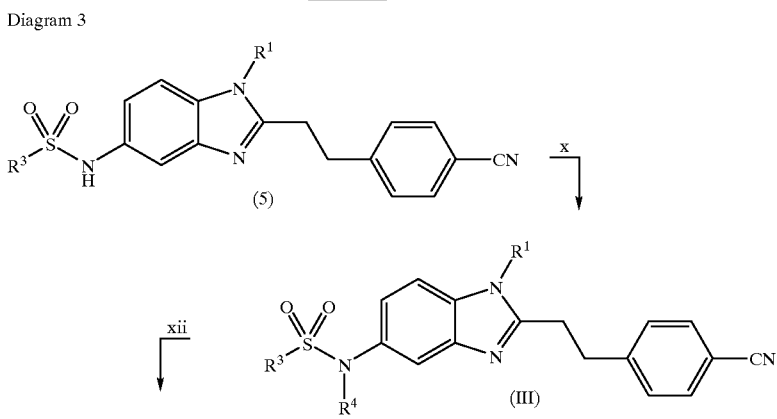

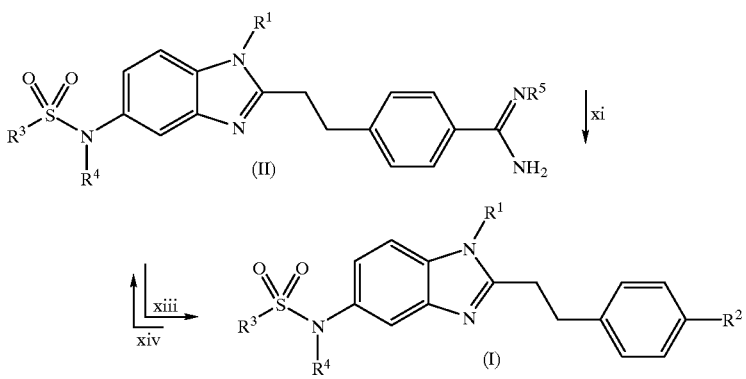

In order to react the compounds (5) with $R^4$-Nu according to step x the following procedure is used. A compound (5) is dissolved in a polar solvent, such as dimethylformamide, dimethylactamide, methylene chloride, tetrahydrofuran, preferably dimethylformamide and most preferably anhydrous, possibly absolute dimethylformamide. The solution thus obtained is combined with a base and the corresponding alkylating agent $R^4$-Nu. The base used may be an alkali or alkaline earth metal carbonate of lithium, sodium, potassium or calcium such as sodium carbonate, lithium carbonate, potassium carbonate, calcium carbonate and preferably potassium carbonate. It is also possible to use the alkali or alkaline earth metal hydroxides of lithium, sodium, potassium, magnesium or calcium, but preferably sodium hydroxide, potassium hydroxide, lithium hydroxide and calcium hydroxide in alcohol or water. The reaction mixture is stirred for 0.5–8 h, preferably 1–4 h at elevated temperature, preferably at 50–120° C., particularly at the reflux temperature of the solvent used. After the reaction is complete the mixture is worked up in the usual way and the crude product obtained is purified by crystallisation or chromatography on silica gel.

If the intermediates (III) are obtained from the compounds (5) by reductive amination, the following procedure is used. The compound (5) is dissolved in a suitable solvent such as for example dichloromethane, dichloroethane, methanol, ethanol, tetrahydrofuran or toluene, and at between 0–60° C., preferably at 20–40° C., the corresponding carbonyl compound is added in the presence of an acid, preferably a carboxylic acid, most preferably a short-chained carboxylic acid, particularly acetic acid. Then a suitable reduction agent is added. Suitable reduction agents which may be used according to the invention are Na[HB(OAc)$_3$], Na[BH$_3$CN], NaBH$_4$, Pd/C—H$_2$, preferably Na[HB(OAc)$_3$]. After working up in the usual way the product is purified by crystallisation or chromatography on silica gel.

According to step xi the compounds of general formula (I) according to the invention may be obtained from the intermediates (III). Various methods may be used to prepare the compounds of general formula (I) according to the invention wherein $R^2$ denotes —C(=NH)NH$_2$.

A compound of general formula (I) is obtained for example by treating a compound of general formula (III) with a corresponding alcohol such as methanol, ethanol, n-propanol, isopropanol or benzylalcohol optionally mixed with another organic solvent such as for example chloroform, nitrobenzene or toluene in the presence of an acid such as hydrochloric acid or by reacting a corresponding amide with a trialkyloxonium salt such as triethyloxonium-tetrafluoroborate in a solvent such as methylene chloride, tetrahydrofuran or dioxan at temperatures between −10 and 50° C., but preferably at 0–20° C. and subsequent aminolysis with alcoholic ammonia solution for example. Alternatively the compounds of general formula (I) may be obtained by reacting a compound of general formula (III) with sulphur nucleophiles such as e.g. hydrogen sulphide, ammonium or sodium sulphide, sodium hydrogen sulphide, carbon disulphide, thioacetamide or bistrimethylsilylthioether, optionally in the presence of bases such as triethylamine, ammonia, sodium hydride or sodium alkoxide in solvents such as methanol, ethanol, water, tetrahydrofuran, pyridine, dimethylformamide or 1,3-dimethyl-imidazolidin-2-one at 20–100° C., and subsequently treating them with a suitable methylating agent such as e.g. methyl iodide or dimethylsulphate in a solvent such as acetonitrile or acetone at temperatures between −10 and 50° C., but preferably at 0–20° C., and then treating them with ammonia, ammonium carbonate or ammonium chloride in a suitable alcohol, such as for example methanol, ethanol, isopropanol etc. at temperatures between −10 and 50° C., but preferably at 0–20° C.

Moreover, the compounds of general formula (I) according to the invention may be obtained by treating a compound of general formula (III) with lithium hexamethyl disilazide in a suitable organic solvent such as e.g. tetrahydrofuran at temperatures between −20 and 50° C., but preferably at 0–20° C. and subsequently hydrolysing with dilute hydrochloric acid at 0–5° C.

Another alternative method of obtaining compounds of general formula (I) is by treating a compound of general formula (III) with ammonium chloride and trimethylaluminium in a suitable organic solvent such as e.g. toluene at temperatures between 20 and 150° C., but preferably at 110° C.

Compounds of general formula (I) wherein $R^2$ denotes —CH$_2$—NH$_2$ may be obtained from the intermediates (III) for example by catalytic hydrogenation on Raney nickel. These reactions are preferably carried out in protic organic solvents such as short-chained alcohols (methanol, ethynol or isopropanol) at temperatures between 10–40° C., preferably at 20–30° C. under normal pressure.

A compound of general formula (II) is obtained for example by treating a compound of general formula (III, Diagram 3, step xii) with hydroxylamine in the presence of carbonates or alkoxides of alkali or alkaline earth metals in solvents such as methanol, ethanol, n-propanol or isopropanol optionally in admixture with dioxan or tetrahydrofuran. The alkoxides may be prepared from the respective alkali metals or metal hydrides and the corresponding alcohol. The reaction is preferably carried out at 20–100° C., most preferably at the boiling temperature of the solvent used.

Compounds of general formula (II) may alternatively be obtained by treating a compound of general formula (III) with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium tetrafluoroborate in a solvent such as methylene chloride, tetrahydrofuran or dioxan at temperatures between −10 and 50° C., but preferably at 0–20° C. and subsequently treating with hydroxylamine in the presence of bases in a suitable alcohol, such as methanol, ethanol, isopropanol etc. at temperatures between −10 and 50° C., but preferably at 0–20° C.

A compound of general formula (I) is obtained for example by treating a compound of general formula (II, Diagram 3, step xiii) with hydrogen in the presence of hydrogenation catalysts such as Raney nickel or rhodium/aluminium oxide in water or methanol optionally with the addition of acids such as hydrochloric acid or methanesulphonic acid or by treating with hydrogen in the presence of palladium/charcoal in acetic acid/acetic anhydride at 20–50° C. and 1–5 bar hydrogen pressure, preferably at ambient temperature and normal pressure.

The acyl- or alkoxycarbonyl prodrugs (II) of the compound of general formula (I) are obtained by reacting the compounds of general formula (I) with the corresponding acid chlorides in the presence of bases such as e.g. triethylamine, N-methyl-morpholine, diethylisopropylamine or DBU in a suitable solvent such as methylene chloride, chloroform, tetrahydrofuran, acetonitrile, dimethylformamide or dimethylsulphoxide.

In accordance with their central role in the synthesis of the compounds of general formula (I) according to the invention as well as the synthesis of the prodrugs of general formula (II), a further aspect of the present invention is directed to the intermediates of general formula (III)

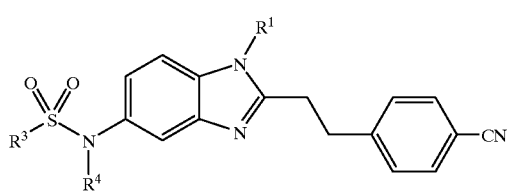

(III)

wherein the groups $R^1$, $R^3$ and $R^4$ may be as hereinbefore defined. The compounds of general formula (III) are valuable intermediates for preparing the benzimidazole derivatives of general formula (I) according to the invention as well as the prodrugs of general formula (II) according to the invention.

On the basis of their pharmacological properties the compounds according to the invention may be used as pharmaceutical compositions, particularly as pharmaceutical compositions with a tryptase-inhibiting effect. They may be used in any circumstances where tryptase inhibitors are able to develop a therapeutic effect.

The compounds of general formula (I) according to the invention are preferably used to prepare a pharmaceutical composition for the prevention and/or treatment of inflammatory and/or allergic diseases. It is particularly preferred to use the compounds of general formula (I) for the purpose mentioned at the beginning, namely for preparing a pharmaceutical composition for the prevention and/or treatment of bronchial asthma, allergic rhinitis, allergic conjunctivitis, atopic dermatitis, urticaria, allergic otitis, allergic gastrointestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasm.

Procedures by way of example for preparing the compounds according to the invention will be described in more detail hereinafter. The Examples which follow serve solely as a detailed illustration without restricting the subject matter of the invention.

EXAMPLE 1

N-{2-[2-(4-amidinophenyl)-ethyl]-1-(3,5-bis-trifluoromethyl-benzyl)-benzimidazol-5-yl}-benzenesulphonamide-hydrochloride

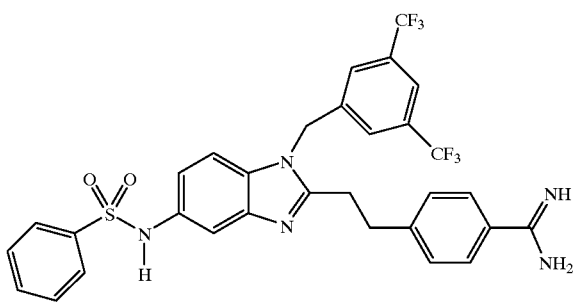

a) N-{4-fluoro-3-nitro-phenyl}-benzenesulphonamide 4-fluoro-3-nitro-aniline (7.8 g, 50 mmol) is taken up in 50 mL pyridine and cooled to 10° C. The benzenesulphonic acid chloride (7.0 mL, about 55 mmol) is added dropwise with stirring within about 20 min at 10–20° C. The mixture is stirred for about 0.5 h at ambient temperature and poured onto ice water. After acidifying with conc. hydrochloric acid the mixture is extracted with 150 mL ethyl acetate, washed with water, dried and concentrated by evaporation. The residue is dissolved in diethylether, diluted with petroleum ether and cooled. The crystals formed are filtered off, washed with diethylether/petroleum ether and dried.

Yield: 12.2 g (82.4%); m.p.: 118–120° C.;

b) N-{3-nitro-4-(3,5-bis-trifluoromethyl-benzylamino)-phenyl}-benzenesulphonamide N-{4-fluoro-3-nitro-phenyl}-benzenesulphonamide (3.0 g, 10 mmol), 3,5-bis-trifluoromethylbenzylamine (3.0 g, 12.5 mmol) and N-methylmorpholine (2.2 mL, 20 mmol) in 25 mL dimethylsulphoxide are kept for 6 h at 60–100° C., diluted with 150 mL ethyl acetate, washed with water, dilute hydrochloric acid and water again, dried and concentrated by evaporation until not quite dry. The residue is combined with 80 mL EtOH and evaporated down to a residual volume of about 50 mL. The crystals precipitated after cooling are filtered off and washed with EtOH and petroleum ether.

Yield: 4.0 g (81.6%); m.p.: 190–193° C.

c) N-{3-amino-4-(3,5-bis-trifluoromethyl-benzylamino)-phenyl}-benzenesulphonamide N-{3-nitro-4-(3,5-bis-trifluoromethyl-benzylamino)-phenyl}-benzenesulphonamide (8.6 g, 16.6 mmol) in 200 mL methanol are refluxed and within 0.5 h combined with a solution of $Na_2S_2O_4$ (14.2 g, mmol) in 50 mL water. The mixture is refluxed until totally decolorised (this takes about 1 h). After cooling the mixture is diluted with water. About 100 mL of the methanol/water mixture are distilled off, the resulting solution is cooled, the crystals precipitated are filtered off and washed with water. The crystals are dissolved in ethyl acetate, dried and evaporated down until not quite dry. After cooling the crystals precipitated are filtered off and washed with diethylether.

Yield: 5.8 g (71.6%); m.p.: 170–172° C.

d) N-{2-[2-(4-Cyanophenyl)-ethyl]-1-(3,5-bis-trifluoromethyl-benzyl)-benzimidazol-5-yl}-benzenesulphonamide N-{3-amino-4-(3,5-bis-trifluoromethyl-benzylamino)-phenyl}-benzenesulphonamide (5.5 g, 11.2 mmol) and p-cyano-phenylpropionic acid (2.35 g, 13.4 mmol) are taken up in 50 mL POCl₃, and stirred for 2 h at 100–120° C. A precipitate settles out from the initially clear solution in the course of the reaction. After cooling it is diluted with 100 mL ethyl acetate/diethylether=1/1. The crystals are filtered off and washed with diethylether.

Yield: 5.35 g (71.5%); m.p.: 140–144° C.

e) N-{2-[2-(4-amidinophenyl)-ethyl]-1-(3,5-bis-trifluoromethyl-benzyl)-benzimidazol-5-yl}-benzenesulphonamide-hydrochloride N-{2-[2-(4-Cyanophenyl)-ethyl]-1-(3,5-bis-trifluoromethyl-benzyl)-benzimidazol-5-yl}-benzenesulphonamide-hydrochloride (1.5 g, 2.3 mmol) is taken up in 50 mL of a saturated ethanolic hydrochloric acid solution cooled to 0° C. It is stirred to dissolve the educt completely and then kept overnight at 0–5° C. The ethanol is distilled off at a maximum of 40° C. and the residue is taken up in 40 mL of a saturated ethanolic ammonia solution at 0° C. It is stirred for 2 h at ambient temperature, 3 h at 50–60°, combined with another 10 mL of saturated NH₃ solution and refluxed for 2 h. It is combined with 20 mL water and 25 mL ethyl acetate and stirred for 0.5 h at ambient temperature. The crystals precipitated are filtered off and washed with ethyl acetate and diethylether.

Yield: 0.9 g (70.3%); m.p.: >220° C.

EXAMPLE 2

N-{2-[2-(4-amidinophenyl)-ethyl]-1-methyl-benzimidazol-5-yl}-N-diethylaminoethyl-(benzenesulphonamide)-dihydrochloride

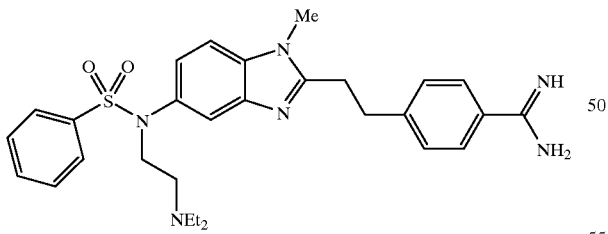

a) N¹-methyl-1,2-diamino-4-nitrobenzene 2-fluoro-5-nitro-aniline (15.0 g, 160 mmol) is taken up in 480 mL of 40% aqueous methylamine solution and stirred for 2.5 days at ambient temperature and for 2 h at 40–50° C. It is diluted with water, the solid is filtered off, washed with water and dried.

Yield: 26 g (97%); m.p.: 171–173° C.

b) 2-[2-(4-Cyanophenyl)-ethyl]-1-methyl-5-nitro-benzimidazole

N¹-methyl-1,2-diamino-4-nitrobenzene (8.3 g, 49.6 mmol) and p-cyano-phenylpropionic acid (9.6 g, 55 mmol) are taken up in 90 mL POCl₃, and refluxed for 1.5 h. After cooling the excess POCl₃ is decomposed with ice water. It is made alkaline with NH₃ with stirring/cooling and stirred for 1 h at ambient temperature. The solid is filtered off, washed with water and recrystallised from DMF.

Yield: 11.7 g (76,4%); m.p.: 202–204° C.

c) 5-amino-2-[2-(4-cyanophenyl)-ethyl]-1-methyl-benzimidazole

2-[2-(4-Cyanophenyl)-ethyl]-1-methyl-5-nitro-benzimidazole (5.5 g, 18 mmol) in 150 mL THF/75 mL methanol is hydrogenated in the presence of 1.0 g of 5% Pd/C at ambient temperature and normal pressure. The catalyst is filtered off, the filtrate is evaporated down until not completely dry, diluted with 100 mL acetonitrile and evaporated down to a residual volume of 30 mL. The crystal slurry is cooled and filtered. The crystals are washed with cold acetonitrile and ether.

Yield: 4.7 g (94%); m.p.: 187–192° C.

d) N-{2-[2-(4-Cyanophenyl)-ethyl]-1-methyl-benzimidazol-5-yl}-(benzenesulphonamide)

5 mmol of 5-amino-2-[2-(4-cyanophenyl)-ethyl]-1-methyl-benzimidazole are reacted to form the title compound in the manner described according to Example 1 (step a).

Yield: 91.3%; m.p.: 222–225° C.

e) N-{2-[2-(4-Cyanophenyl)-ethyl]-1-methyl-benzimidazol-5-yl}-N-diethylaminoethyl-(benzenesulphonamide)

N-{2-[2-(4-Cyanophenyl)-ethyl]-1-methyl-benzimidazol-5-yl}-(benzenesulphonamide) (5.9 mmol), diethylaminoethyl chloride (7.0 mmol), 4.0 g of K₂CO₃ and catalytic quantities of KI are refluxed in 50 mL dimethylformamide for 1.5 h. After cooling the mixture is poured onto ice water, extracted with 100 mL ethyl acetate, dried and concentrated by evaporation. The residue is filtered with 95/5 CH₂Cl₂/methanol through a dry packed silica gel column. After evaporation the residue is crystallised from ethyl acetate and diethylether.

Yield: 78.5%; m.p.: 120–122° C.

f) N-{2-[2-(4-amidinophenyl)-ethyl]-1-methyl-benzimidazol-5-yl}-N-diethylaminoethyl-(benzenesulphonamide)-dihydrochloride The title compound is prepared starting from 2.7 mmol of N-{2-[2-(4-cyanophenyl)-ethyl]-1-methyl-benzimidazol-5-yl}-N-diethylaminoethyl-(benzenesulphonamide) analogously to the method described in Example 1 (step e).

Yield: 70.1% (amorphous solid); Mass: calc.: [532], found: [M+H]⁺ 533, [M+2H]²⁺ 267.

EXAMPLE 3

N-{2-[2-(4-amidinophenyl)-ethyl]-1-(3-ethoxy-propyl)-benzimidazol-5-yl}-N-diethylaminoethyl-(benzenesulphonamide)-dihydrochloride

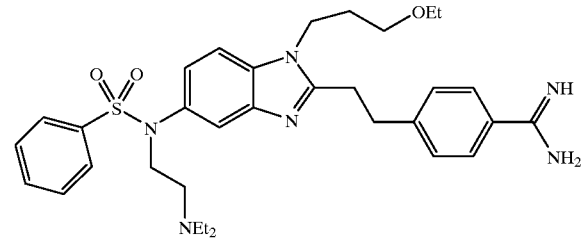

a) N¹-(3-ethoxy-propyl)-1,2-diamino-4-nitro-benzene 2-fluoro-5-nitro-aniline (5.0 g, 32 mmol) and 3-ethoxypropylamine (11.5 mL, 96 mmol) in 15 mL dimethylsulphoxide are stirred for 10 h at 100–110° C. The mixture is diluted with 100 mL ethyl acetate, washed 2× with water, dried and concentrated by evaporation. The product is crystallised from ethyl acetate/diethylether.

Yield: 6.1 g (79.7%); m.p.: 69–70° C.

b) 2-[2-(4-Cyanophenyl)-ethyl]-1-(3-ethoxy-propyl)-5-nitro-benzimidazole 25.3 mmol of $N^1$-(3-ethoxy-propyl)-1,2-diamino-4-nitro-benzene are reacted to form the title compound in the manner described according to Example 2 (step b). For working up the mixture is poured onto ice water, covered with ethyl acetate, made alkaline with aqueous ammonia solution and extracted. Crystals from ethyl acetate.

Yield: 76.0%; m.p.: 112–114° C.

c) 5-amino-2-[4-cyanomethyl-phenyl]-1-(3-ethoxy-propyl)-benzimidazole 20 mmol of 2-[4-cyanomethyl-phenyl]-1-(3-ethoxy-propyl)-5-nitro-benzimidazole are reacted to form the title compound in the manner described according to Example 2 (step c). The substance is crystallised from ethyl acetate/diethylether.

d) N-{2-[4-Cyanomethyl-phenyl]-1-(3-ethoxy-propyl)-benzimidazol-5-yl}-(benzenesulphonamide) 6 mmol of 5-amino-2-[4-cyanomethyl-phenyl]-1-(3-ethoxy-propyl)-benzimidazole are reacted to form the title compound in the manner described according to Example 1 (step a).

Yield: 85.3%.

e) N-{2-[2-(4-Cyanophenyl)-ethyl]-1-(3-ethoxy-propyl)-benzimidazol-5-yl}-N-diethylaminoethyl-(benzenesulphonamide)

6 mmol of N-{2-[2-(4-cyanophenyl)-ethyl]-1-(3-ethoxy-propyl)-benzimidazol-5-yl}-(benzenesulphonamide) are reacted to form the title compound in the manner described according to Example 2 (step e).

Yield: 71%.

f) N-{2-[2-(4-amidinophenyl)-ethyl]-1-(3-ethoxy-propyl)-benzimidazol-5-yl}-N-diethylaminoethyl-(benzenesulphonamide)-dihydrochloride 6 mmol of N-{2-[2-(4-cyanophenyl)-ethyl]-1-(3-ethoxy-propyl)-benzimidazol-5-yl}-N-diethylaminoethyl-(benzenesulphonamide) are reacted to form the title compound in the manner described according to Example 2 (step f).

Yield: 40.5%; Mass: calc.: [604], found: [M+H]$^+$ 605, [M+2H]$^{2+}$ 303.

EXAMPLE 4

N-{2-[2-(4-amidinophenyl)-ethyl]-1-methyl-benzimidazol-5-yl}-N-(4-dimethylaminobenzyl)-(benzenesulphonamide)-dihydrochloride

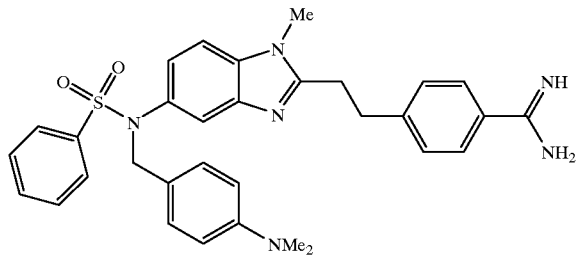

a) 2-[2-(4-Cyanophenyl)-ethyl]-1-methyl-5-(4-dimethylaminobenzylamino)-benzimidazole 5-amino-2-[2-(4-cyanophenyl)-ethyl]-1-methyl-benzimidazole (1.0 g, 3.6 mmol) which is obtainable according to Example 2 (step c) and 4-dimethylamino-benzaldehyde (0.59 g, 3.0 mmol) in 25 mL of $CH_2Cl_2$ with 0.22 mL of AcOH are combined with Na[HB(OAc)$_3$](2.2 g, 10.3 mmol) at ambient temperature with stirring. The mixture is stirred for 1 h at ambient temperature, covered with water, carefully acidified with conc hydrochloric acid$_{aq}$ and then made alkaline with 4N NaOH solution. The organic phase is separated off, dried and concentrated by evaporation. The product is chromatographed over silica gel ($CH_2Cl_2$/methanol=5/1) and crystallised from ethyl acetate.

Yield: 1.2 g (81%).

b) N-{2-[2-(4-amidinophenyl)-ethyl]-1-methyl-benzimidazol-5-yl}-N-(4-dimethylaminobenzyl)-(benzenesulphonamide)-dihydrochloride 2.8 mmol of 2-[2-(4-cyanophenyl)-ethyl]1-methyl-5-(4-dimethylaminobenzylamino)-benzimidazole are reacted to form the title compound according to the instructions given in Example 1 (step a) and Example 1 (step e).

Yield: 39% (solid foam); Mass: calc.: [566], found: [M+H]$^+$ 567, [M+2H]$^{2+}$) 284.

EXAMPLE 5

N-{2-[2-(4-aminomethyl-phenyl)-ethyl]-1-methyl-benzimidazol-5-yl}-N-diethylaminoethyl-(benzenesulphonamide)-dihydrochloride

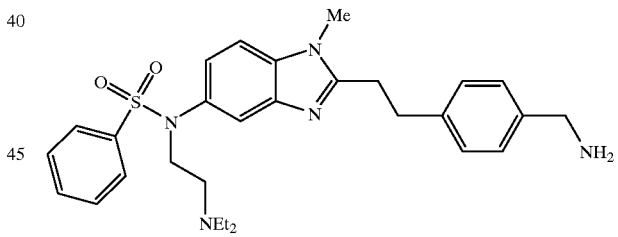

N-{2-[2-(4-Cyanophenyl)-ethyl]-1-methyl-benzimidazol-5-yl}-N-diethylaminoethyl-(benzenesulphonamide) (obtainable according to Example 2, step e) (1.6 g, 3.1 mmol) in 50 mL methanol is hydrogenated at ambient temperature and normal pressure in the presence of Raney nickel. The catalyst is filtered off and the filtrate is neutralised by the addition of ethereal hydrochloric acid solution. It is concentrated by evaporation and chromatographed over silica gel ($CH_2Cl_2$/methanol=7/3).

Yield: 1.0 g (54.5%); Mass: calc.: [519], found: [M+H]$_+$ 520.

TABLE 1

The Table which follows contains other compounds of general formula (I) synthesised according to the invention analogously to the Examples described hereinbefore.

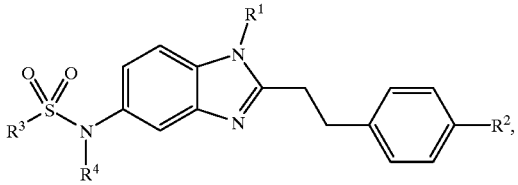

| No | —R¹ | —R² | —R³ | —R⁴ | Chemical name |
|---|---|---|---|---|---|
| 6 | —methyl | 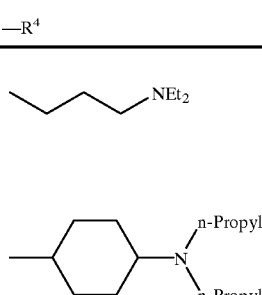 | phenyl | 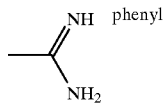 | 1-methyl-2-[2-(4-aminophenyl)-ethyl]-5-[N-(3-diethylamino-propyl)-benzenesulphonyl-amino]-benzimidazole |
| 7 | —methyl | 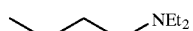 | phenyl | 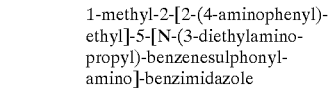 | 1-methyl-2-[2-(4-amidino-phenyl)-ethyl]-5-[N-(4-dipropyl-amino-cyclohexanyl)-benzene-sulphonyl-amino]-benzimidazole |
| 8 | —methyl | 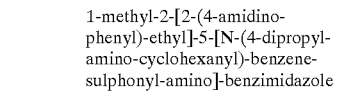 | phenyl | 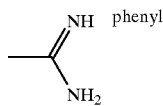 | 1-methyl-2-[2-(4-amidino-phenyl)-ethyl]-5-[N-(1-methyl-pyrrolidin-3-yl-methyl)-benzene-sulphonyl-amino]-benzimidazole |
| 9 | —methyl | 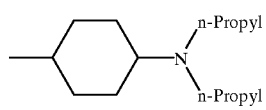 | phenyl | 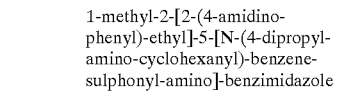 | 1-methyl-2-[2-(4-amidino-phenyl)-ethyl]-5-[N-(1-methyl-pyrrolidin-2-yl-methyl)-benzene-sulphonyl-amino]-benzimidazole |
| 10 | —methyl | 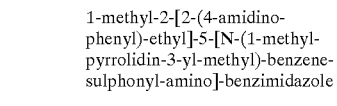 | phenyl | 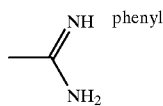 | 1-methyl-2-[2-(4-amidino-phenyl)-ethyl]-5-[N-(1-benzyl-pyrrolidin-3-yl-methyl)-benzene-sulphonyl-amino]-benzimidazole |
| 11 | —methyl | 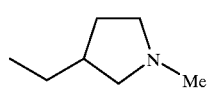 | phenyl | 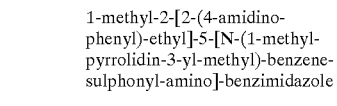 | 1-methyl-2-[2-(4-amidino-phenyl)-ethyl]-5-[N-(4-piperidinyl)-benzenesulphonyl-amino]-benzimidazole |
| 12 | —methyl | 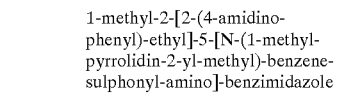 | phenyl | 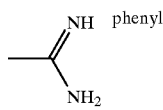 | 1-methyl-2-[2-(4-amidino-phenyl)-ethyl]-5-[N-(1-methyl-piperidin-4-yl)-benzene-sulphonylamino]-benzimidazole |
| 13 | —methyl | 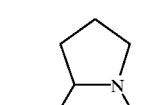 | phenyl | 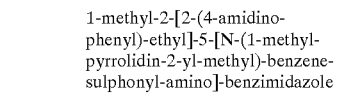 | 1-methyl-2-[2-(4-amidino-phenyl)-ethyl]-5-[N-(1-benzyl-piperidin-4-yl)-benzene-sulphonylamino]-benzimidazole |
| 14 | —methyl | 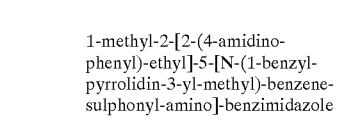 | phenyl | 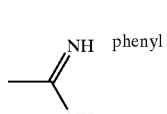 | 1-methyl-2-[2-(4-amidino-phenyl)-ethyl]-5-[N-(3-pyrrolidinyl)-benzenesulphonyl-amino]-benzimidazole |
| 15 | —methyl | 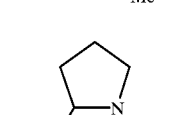 | phenyl | 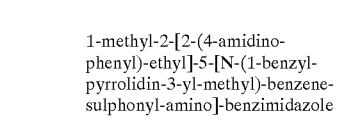 | 1-methyl-2-[2-(4-amidino-phenyl)-ethyl]-5-[N-(4-amidino-benzyl)-benzenesulphonyl-amino]-benzimidazole |

TABLE 1-continued

The Table which follows contains other compounds of general formula (I) synthesised according to the invention analogously to the Examples described hereinbefore.

(I)

| No | —R¹ | —R² | —R³ | —R⁴ | Chemical name |
|---|---|---|---|---|---|
| 16 | —CH₂CH₂OH | 4-amidino (C(=NH)NH₂) | phenyl | —CH₂CH₂NEt₂ | 1-(2-hydroxyethyl)-2-[2-(4-amidinophenyl)-ethyl]-5-[N-(2-diethylaminoethyl)-benzene-sulphonylamino]-benzimidazole |
| 17 | —CH₂CH₂OMe | 4-amidino | phenyl | —CH₂CH₂NEt₂ | 1-(2-methoxyethyl)-2-[2-(4-amidinophenyl)-ethyl]-5-[N-(2-diethylaminoethyl)-benezene-sulphonylamino]-benzimidazole |
| 18 | —n-propyl | 4-amidino | phenyl | —CH₂CH₂NEt₂ | 1-n-propyl-2-[2-(4-amidinophenyl)-ethyl]-5-[N-(2-diethylaminoethyl)-benzenesulphonylamino]-benzimidazole |
| 19 | —(CH₂)₃OH | 4-amidino | phenyl | —CH₂CH₂NEt₂ | 1-(3-hydroxypropyl)-2-[2-(4-amidinophenyl)-ethyl]-5-[N-(2-diethylaminoethyl)-benzene-sulphonylamino]-benzimidazole |
| 20 | isoamyl (—CH₂CH₂CH(Me)Me) | 4-amidino | phenyl | —CH₂CH₂NEt₂ | 1-isoamyl-2-[2-(4-amidinophenyl)-ethyl]-5-[N-(2-diethylaminoethyl)-benzenesulphonyl-amino]-benzimidazole |
| 21 | 4-carboxybenzyl | 4-amidino | phenyl | —CH₂CH₂NEt₂ | 1-(4-carboxybenzyl)-2-[2-(4-amidinophenyl)-ethyl]-5-[N-(2-diethylaminoethyl)-benzene-sulphonylamino]-benzimidazole |
| 22 | 4-ethoxycarbonylbenzyl | 4-amidino | phenyl | —CH₂CH₂NEt₂ | 1-(4-ethoxycarbonylbenzyl)-2-[2-(4-amidinophenyl)-ethyl]-5-[N-(2-diethylaminoethyl)-benzenesulphonylamino]-benzimidazole |
| 23 | 3,5-bis(trifluoromethyl)benzyl | 4-amidino | phenyl | —CH₂CH₂NEt₂ | 1-(3,5-Ditrifluoromethylbenzyl)-2-[2-(4-amidinophenyl)-ethyl]-5-[N-(2-diethylaminoethyl)-benzenesulphonylamino]-benzimidazole |
| 24 | 2-phenylethyl | 4-amidino | phenyl | —CH₂CH₂NEt₂ | 1-(2-phenylethyl)-2-[2-(4-amidinophenyl)-ethyl]-5-[N-(2-diethylaminoethyl)-benzene-sulphonylamino]-benzimidazole |

TABLE 1-continued

The Table which follows contains other compounds of general formula (I) synthesised according to the invention analogously to the Examples described hereinbefore.

| No | —R¹ | —R² | —R³ | —R⁴ | Chemical name |
|---|---|---|---|---|---|
| 25 | 3-phenylpropyl | 4-amidinophenyl (C(=NH)NH₂) | phenyl | —CH₂CH₂NEt₂ | 1-(3-phenylpropyl)-2-[2-(4-amidinophenyl)-ethyl]-5-[N-(2-diethylaminoethyl)-benzene-sulphonylamino]-benzimidazole |
| 26 | 2-(2-methoxyphenoxy)ethyl | 4-amidinophenyl | phenyl | —CH₂CH₂NEt₂ | 1-[2-(2-methoxyphenoxy)ethyl]-2-[2-(4-amidinophenyl)-ethyl]-5-[N-(2-diethylaminoethyl)-benzenesulphonylamino]-benzimidazole |
| 27 | 2-tetrahydrofurylmethyl | 4-amidinophenyl | phenyl | —CH₂CH₂NEt₂ | 1-(2-tetrahydrofurylmlethyl)-2-[2-(4-amidinophenyl)-ethyl]-5-[N-(2-diethylaminoethyl)-benzenesulphonylamino]-benzimidazole |
| 28 | —methyl | 4-amidinophenyl | 1-naphthyl | —CH₂CH₂NEt₂ | 1-methyl-2-[2-(4-amidino-phenyl)-ethyl]-5-[N-(2-diethyl-aminoethyl)-naphth-1-yl-sulphonylamino]-benzimidazole |
| 29 | 2-hydroxypropyl | 4-amidinophenyl | phenyl | —CH₂CH₂NEt₂ | 1-(2-hydroxypropyl)-2-[2-(4-amidinophenyl)-ethyl]-5-[N-(2-diethylaminoethyl)-benzene-sulphonylamino]-benzimidazole |
| 30 | 2,3-dihydroxypropyl | 4-amidinophenyl | phenyl | —CH₂CH₂NEt₂ | 1-(2,3-dihydroxypropyl)-2-[2-(4-amidinophenyl)-ethyl]-5-[N-(2-diethylaminoethyl)-benzene-sulphonylamino]-benzimidazole |
| 31 | —methyl | 4-amidinophenyl | phenyl | —CH₂CH₂-(azepin-1-yl) | 1-methyl-2-[2-(4-amidino-phenyl)-ethyl]-5-[N-(2-azepin-1-ylethyl)-benzenesulphonyl-amino]-benzimidazole |
| 32 | —methyl | 4-amidinophenyl | phenyl | —CH₂CH₂-(morpholin-4-yl) | 1-methyl-2-[2-(4-amidino-phenyl)-ethyl]-5-[N-(2-morpholin-4-ylethyl)-benzene-sulphonyl-amino]-benzimidazole |
| 33 | —methyl | 4-amidinophenyl | phenyl | —CH₂CH₂-(piperidin-1-yl) | 1-methyl-2-[2-(4-amidino-phenyl)-ethyl]-5-[N-(2-piperidin-1-ylethyl)-benzene-sulphonylamino]-benzimidazole |
| 34 | —methyl | 4-amidinophenyl | phenyl | —CH₂CH₂-(pyrrolidin-1-yl) | 1-methyl-2-[2-(4-amidino-phenyl)-ethyl]-5-[N-(2-pyrrolidin-1-ylethyl)-benzene-sulphonylamino]-benzimidazole |

TABLE 1-continued

The Table which follows contains other compounds of general formula (I) synthesised according to the invention analogously to the Examples described hereinbefore.

(I)

| No | —R$^1$ | —R$^2$ | —R$^3$ | —R$^4$ | Chemical name |
|---|---|---|---|---|---|
| 35 | —methyl | amidino (—C(NH)NH$_2$) | 2-naphthyl | —CH$_2$CH$_2$NEt$_2$ | 1-methyl-2-[2-(4-amidino-phenyl)-ethyl]-5-[N-(2-diethylaminoethyl)-naphth-2-yl-sulphonylamino]-benzimidazole |
| 36 | —methyl | amidino | phenyl | —CH$_2$C(O)-N(piperazinyl)-(2-pyridyl) | N-{2-[(2-(4-amidino-phenyl)-ethyl]-1-methyl-benzimidazol-5-yl}-N-[4'-(pyrid-2-yl)-piperazyl-carbonylmethyl]-(benzene-sulphonamide) |
| 37 | —methyl | amidino | Benzyl | —CH$_2$CH$_2$NEt$_2$ | 1-methyl-2-[2-(4-amidino-phenyl)-ethyl]-5-[N-(2-diethylaminoethyl)-benzyl-sulphonylamino]-benzimidazole |
| 38 | —CH$_2$CH$_2$CONHMe | amidino | Phenyl | —CH$_2$CH$_2$NEt$_2$ | 1-(2-Methylaminocarbonyl-ethyl)-2-[2-(4-amidinophenyl)-ethyl]-5-[N-(2-diethylamino-ethyl)-benzenesulphonylamino]-benzimidazole |
| 39 | —CH$_2$CH$_2$CONH$_2$ | amidino | Phenyl | —CH$_2$CH$_2$NEt$_2$ | 1-(2-Aminocarbonyl-ethyl)-2-[2-(4-amidinophenyl)-ethyl]-5-[N-(2-diethylaminoethyl)-benzene-sulphonylamino]-benzimidazole |
| 40 | —CH$_2$CONH$_2$ | amidino | Phenyl | —CH$_2$CH$_2$NEt$_2$ | 1-Aminocarbonylmethyl-2-[2-(4-amidinophenyl)-ethyl]-5-[N-(2-diethylaminoethyl)-benzene-sulphonylamino]-benzimidazole |
| 42 | Methyl | amidino | Phenyl | Methyl | 1-Methyl-2-[2-(4-amidino-phenyl)-ethyl]-5-N-methyl-benzene-sulphonylamino]-benzimidazole |
| 43 | Methyl | amidino | Benzo[b]-thien-3-yl | —CH$_2$CH$_2$NEt$_2$ | 1-Methyl-2-[2-(4-amidino-phenyl)-ethyl]-5-[N-(2-diethyl-aminoethyl)-benzo[b]thien-3-yl-sulphonylamino]-benzimidazole |
| 44 | Methyl | amidino | Naphth-2-yl | —CH$_2$-(pyrid-2-yl) | 1-Methyl-2-[2-(4-amidino-phenyl)-ethyl]-5-[N-(pyrid-2-yl-methyl)-naphth-2-ylsulphonyl-amino]-benzimidazole; |
| 45 | Methyl | amidino | Naphth-2-yl | —CH$_2$-(pyrid-3-yl) | 1-Methyl-2-[2-(4-amidino-phenyl)-ethyl]-5-[N-(pyrid-3-yl-methyl)-naphth-2-ylsulphonyl-amino]-benzimidazole; |

TABLE 1-continued

The Table which follows contains other compounds of general formula (I) synthesised according to the invention analogously to the Examples described hereinbefore.

(I)

| No | —R¹ | —R² | —R³ | —R⁴ | Chemical name |
|----|-----|-----|-----|-----|---------------|
| 46 | Methyl | –C(=NH)NH₂ | Naphth-2-yl | piperidine-N-CH₂-C₆H₅ acyl | 1-Methyl-2-[2-(4-amidino-phenyl)-ethyl]-5-[N-(4'-benzyl-piperid-1-yl-carbonylmethyl)-naphth-2-ylsulphonylamino]-benzimidazole |
| 47 | Methyl | –C(=NH)NH₂ | Naphth-2-yl | morpholinoethyl | 1-Methyl-2-[2-(4-amidino-phenyl)-ethyl]-5-[N-(2-morpholinoethyl)-naphth-2-yl-sulphonylamino]-benzimidazole |
| 48 | Methyl | –C(=NH)NH₂ | Naphth-2-yl | piperazine-N-acyl | 1-Methyl-2-[2-(4-amidino-phenyl)-ethyl]-5-[N-(piperazin-1-yl-carbonylmethyl)-naphth-2-ylsulphonylamino]-benzimidazole |
| 49 | Methyl | –C(=NH)NH₂ | Naphth-2-yl | 4-pyrid-4-yl-piperazin-1-yl-carbonyl-methyl | 1-Methyl-2-[2-(4-amidino-phenyl)-ethyl]-5-[N-(4'-pyrid-4''-yl-piperazin-1-yl-carbonyl-methyl)-naphth-2-ylsulphonyl-amino]-benzimidazole |
| 50 | Methyl | –C(=NH)NH₂ | Naphth-2-yl | 4-benzyl-piperazin-1-yl-carbonyl-methyl | 1-Methyl-2-[2-(4-amidino-phenyl)-ethyl]-5-[N-(4'-benzyl-piperazin-1-yl-carbonylmethyl)-naphth-2-ylsulphonylamino]-benzimidazole |
| 51 | Methyl | –C(=NH)NH₂ | Naphth-2-yl | 4-(3-hydroxypropyl)-piperazin-1-yl-carbonyl-methyl | 1-Methyl-2-[2-(4-amidino-phenyl)-ethyl]-5-[N-(4'-(3''-hydroxypropyl)-piperazin-1-yl-carbonylmethyl)-naphth-2-yl-sulphonylamino]-benzimidazole |
| 52 | Methyl | –C(=NH)NH₂ | Quinol-8-yl | –CH₂CH₂NEt₂ | 1-Methyl-2-[2-(4-amidino-phenyl)-ethyl]-5-[N-(2-diethyl-aminoethyl)-quinol-8-yl-sulphonylamino]-benzimidazole; |
| 53 | Methyl | –C(=NH)NH₂ | Isoquinol-5-yl | –CH₂CH₂NEt₂ | 1-Methyl-2-[2-(4-amidino-phenyl)-ethyl]-5-[N-(2-diethyl-aminoethyl)-isoquinol-5-yl-sulphonylamino]-benzimidazole; |
| 54 | Methyl | –C(=NH)NH₂ | Phenyl | –(CH₂)₄NMe₂ | 1-Methyl-2-[2-(4-amidino-phenyl)-ethyl]-5-[N-(4-dimethyl-aminobutyl)-benzenesulphonyl-amino]-benzimidazole |
| 55 | Methyl | –C(=NH)NH₂ | Phenyl | 4-methyl-1,4-diazepin-1-yl-carbonyl-methyl | 1-Methyl-2-[2-(4-amidino-phenyl)-ethyl]-5-[N-(4-methyl-1,4-diazepin-1-yl-carbonyl-methyl)-benzenesulphonyl-amino]-benzimidazole |

EXAMPLE 56

N-{2-[2-(4-(amino-hydroximinomethyl)-phenyl)-ethyl]-1-methyl-benzimidazol-5-yl}-N-[2-(morpholin-4-yl)-ethyl]-(benzenesulphonamide)

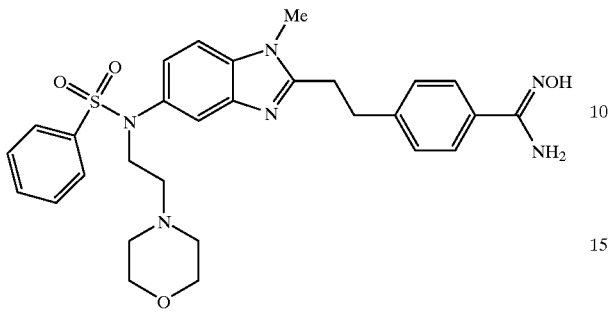

a) N-{2-[2-(4-(amino-hydroximinomethyl)-phenyl)-ethyl]-1-methyl-benzimidazol-5-yl}-(benzenesulphonamide)

3 mmol of N-{2-[2-(4-cyanophenyl)-ethyl]-1-methyl-benzimidazol-5-yl}-(benzenesulphonamide), which may be obtained according to Example 2 (step d), $NH_2OH*HCl$ (1.3 g) and $Na_2CO_3$ (2.2 g) in 50 mL methanol/tetrahydrofuran are refluxed for 2 h. The solvent is distilled off, the residue is taken up in water, extracted with ethyl acetate and combined with water. The crystals precipitated are suction filtered and washed with ethyl acetate, acetonitrile and diethylether. Yield: 84% b) N-{2-[2-(4-(amino-hydroximinomethyl)-phenyl)-ethyl]-1methyl-benzimidazol-5-yl}-N-(morpholin-1-yl-ethyl-(benzenesulphonamide)

Starting from 5 mmol of N-{2-[2-(4-(amino-hydroximinomethyl)-phenyl)-ethyl]-1methyl-benzimidazol-5-yl}-(benzenesulphonamide) the title compound is synthesised by reacting with N-(2-chloroethyl)-morpholine analogously to Example 2 (step e).

Yield: 64%; m.p.: 183–186° C. Mass: calc.: [562], found: $[M+H]^+$ 563, $[M+2H]^{2+}$ 282.

EXAMPLE 57

N-{2-[2-(4-(amino-benzoylimino-methyl)-phenyl)-ethyl]-1-methyl-benzimidazol-5-yl}-N-diethylaminoethyl-(benzenesulphonamide)

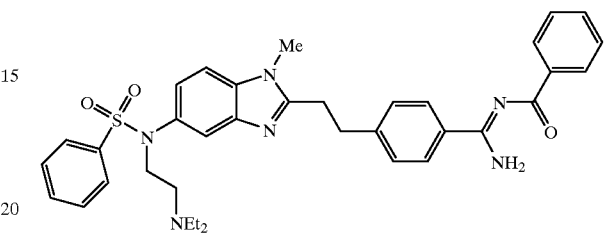

N-{2-[2-(4-amidinophenyl)-ethyl]-1-methyl-benzimidazol-5-yl}-N-diethylaminoethyl-(benzenesulphonamide) (Example 2, 2.0 g, 3.0 mmol) and TEA (0.6 mL, 6.0 mmol) in 100 mL ethyl acetate/$CH_2Cl_2$ 1/1 are combined with benzoyl chloride (0.5 mL, 3.3 mmol) at ambient temperature with stirring. The mixture is stirred for 2 h at ambient temperature, diluted with 50 mL $CH_2Cl_2$, washed with water, dried and concentrated by evaporation. The product is purified by chromatography over silica gel ($CH_2Cl_2$/methanol=10/1).

Yield. 1.0 g (47.6%); Mass: calc.: [636], found: $[M+H]^+$ 637.

TABLE 2

The Table which follows contains other produrgs of general formula (II) synthesised according to the invention analogously to the Examples described hereinbefore.

(II)

| No | —$R^1$ | —$R^3$ | —$R^4$ | —$R^5$ | Chemical name |
|---|---|---|---|---|---|
| 58 | —Methyl | Phenyl | ethyl-phenyl-C(=NOH)NH$_2$ group | —OH | N-{2-[2-(4-(Amino-hydroximinomethyl)-phenyl)-ethyl]-1-methyl-benzimidazol-5-yl}-N-(4-(aminohydroximino-methyl)-benzyl)-(benzene-sulphonamide) |

TABLE 2-continued

The Table which follows contains other prodrugs of general formula (II) synthesised according to the invention analogously to the Examples described hereinbefore.

(II)

| No | —R¹ | —R³ | —R⁴ | —R⁵ | Chemical name |
|---|---|---|---|---|---|
| 59 | (tetrahydrofuran-2-ylmethyl) | Phenyl | —CH₂CH₂—NEt₂ | —OH | N-{2-[2-(4-(Amino-hydroximinomethyl)-phenyl)-ethyl]-1-(tetrahydrofuran-2-yl-methyl)-benzimidazol-5-yl}-N-diethylaminoethyl-(benzene-sulphonamide) |
| 60 | —CH₂CH₂OH (shown as propyl-OH) | Phenyl | —CH₂CH₂—NEt₂ | —OH | N-{2-[2-(4-(Amino-hydroximinomethyl)-phenyl)-ethyl]-1-(2-hydroxyethyl)-benzimidazol-5-yl}-N-diethylaminoethyl-(benzene-sulphonamide) |
| 61 | —CH₂CH₂OMe | Phenyl | —CH₂CH₂—NEt₂ | —OH | N-{2-[4-(4-(Amino-hydroximinomethyl)-phenyl]-1-(2-methoxy-ethyl)-benzimidazol-5-yl}-N-diethyl-aminoethyl-(benzenesulphonamide) |
| 62 | —CH₂CH₂CH₂OH | Phenyl | —CH₂CH₂—NEt₂ | —OH | N-{2-[2-(4-(Amino-hydroximinomethyl)-phenyl)-ethyl]-1-(3-hydroxypropyl)-benzimidazol-5-yl}-N-diethyl-aminoethyl-(benzene-sulphonamide) |
| 63 | —CH(Me)CH₂OH (2-hydroxypropyl) | Phenyl | —CH₂CH₂—NEt₂ | —OH | N-{2-[2-(4-(Amino-hydroximinomethyl)-phenyl)-ethyl]-1-(2-hydroxypropyl)-benzimidazol-5-yl}-N-diethyl-aminoethyl-(benzene-sulphonamide) |
| 64 | —Methyl | 2-Naphthyl | —CH₂CH₂—NEt₂ | —OH | N-{2-[2-(4-(Amino-hydroximinomethyl)-phenyl)-ethyl]-1-methyl-benzimidazol-5-yl}-N-diethylaminoethyl-(2-naphthylsulphonamide) |
| 65 | 2-(2-methoxy-phenyloxy)-ethyl | Phenyl | —CH₂CH₂—NEt₂ | —OH | N-{2-[2-(4-(Amino-hydroximinomethyl)-phenyl)-ethyl]-1-[2-(2-methoxy-phenyloxy)-ethyl]-benzimidazol-5-yl}-N-diethylaminoethyl-(benzenesulphonamide) |
| 66 | —Methyl | Phenyl | —CH₂C(O)—N(piperazinyl)-2-pyridyl | —OH | N-{2-[2-(4-(Amino-hydroximinomethyl)-phenyl)-ethyl]-1-methyl-benzimidazol-5-yl}-N-[4'-(pyrid-2-yl)-piperazyl-carbonylmethyl]-(benzenesulphonamide) |

TABLE 2-continued

The Table which follows contains other produrgs of general formula (II) synthesised according to the invention analogously to the Examples described hereinbefore.

(II)

| No | —R¹ | —R³ | —R⁴ | —R⁵ | Chemical name |
|----|-----|-----|-----|-----|---------------|
| 67 | —Methyl | Phenyl | (azepan-1-yl-ethyl) | —OH | N-{2-[2-(4-(Amino-hydroximinomethyl)-phenyl)-ethyl]-1 methyl-benzimidazol-5-yl}-N-(azepan-1-yl-ethyl)-(benzenesulphonamide) |
| 68 | —Methyl | Phenyl | (piperidin-1-yl-ethyl) | —OH | N-{2-]2-(4-(Amino-hydroximinomethyl)-phenyl)-ethyl]-1 methyl-benzimidazol-5-yl}-N-(piperidin-1-yl-ethyl)-(benzenesulphonamide) |
| 69 | —Methyl | Phenyl | (pyrrolidin-1-yl-ethyl) | —OH | N-{2-[2-(4-Amino-hydroximino-methyl)-phenyl)-ethyl]-1 methyl-benzimidazol-5-yl}-N-(pyrrolidin-1-yl-ethyl)-(benzenesulphonamide) |
| 70 | 2,3-dihydroxypropyl (OH, OH) | Phenyl | —NEt₂ ethyl | —OH | N-{2-[2-(4-(Amino-hydroximinomethyl)-phenyl)-ethyl]-1-(2,3-dihydroxypropyl)-benzimidazol-5-yl}-N-diethyl-aminoethyl-(benzenesulphon-amide) |
| 71 | —CONHMe ethyl | Phenyl | —NEt₂ ethyl | —OH | N-{2-[2-(4-(Amino-hydroximinomethyl)-phenyl)-ethyl]-1-(2-methylamino-carbonylethyl)-benzimidazol-5-yl}-N-diethylaminoethyl-(benzenesulphonamide) |
| 72 | —CONH₂ ethyl | Phenyl | —NEt₂ ethyl | —OH | N-{2-[2-(4-(Amino-hydroximinomethyl)-phenyl)-ethyl]-1-(2-aminocarbonyl-ethyl)-benzimidazol-5-yl}-N-diethylaminoethyl-(benzene-sulphonamide) |
| 73 | —CONH₂ methyl | Phenyl | —NEt₂ ethyl | —OH | N-{2-[2-(4-Amino-hydroximinomethyl)-phenyl)-ethyl]-1-(aminocarbonylmethyl)-benzimidazol-5-yl}-N-diethyl-aminoethyl-(benzene-sulphonamide) |
| 74 | —Methyl | Phenyl | —Methyl | —OH | N-{2-[2-(4-(Amino-hydroximinomethyl)-phenyl)-ethyl]-1-methyl}-benzimidazol-5-yl}-N-diethylaminoethyl-(benzene-sulphonamide) |

TABLE 2-continued

The Table which follows contains other produrgs of general formula (II) synthesised according to the invention analogously to the Examples described hereinbefore.

(II)

| No | —R¹ | —R³ | —R⁴ | —R⁵ | Chemical name |
|----|-----|-----|-----|-----|---------------|
| 75 | —Methyl | Phenyl | —CH₂CH₂—NEt₂ | —COOMe | N-{2-[2-(4-(Amino-methoxy-carbonylimino-methyl)-phenyl)-ethyl]-1-methyl-benzimidazol-5-yl}-N-diethyl-aminoethyl-(benzene-sulphonamide) |
| 76 | —Methyl | Phenyl | —CH₂CH₂—NEt₂ | —C(=O)O—CH₂—CH(Me)—Me | N-{2-[2-(4-(Amino-isobutoxy-carbonylimino-methyl)-phenyl)-ethyl]-1-methyl-benzimidazol-5-yl}-N-diethylaminoethyl-(benzenesulphonamide) |
| 77 | —Methyl | Phenyl | —CH₂CH₂—NEt₂ | —C(=O)-(3-pyridyl) | N-{2-[2-(4-Amino-nicotinoyl-imino-methyl)-phenyl)-ethyl]-1-methyl-benzimidazol-5-yl}-N-diethylaminoethyl-(benzene-sulphonamide) |
| 78 | —Methyl | Phenyl | —CH₂CH₂—NEt₂ | —C(=O)O—CH₂CH₂—Me | N-{2-[2-(4-Amino-n-propoxy-carbonylimino-methyl)-phenyl)-ethyl]-1-methyl-benzimidazol-5-yl}-N-diethylaminoethyl-(benzenesulphonamide) |

The structure of the compounds of general formula (I) according to the invention as well as that of the prodrugs of general formula (II) was confirmed by $^1$-H-NMR spectroscopy.

EXAMPLE 1

$^1$H-NMR (250 MHz, DMSO-d6): δ=10.08 (1H, s, NH); 9.31; 9.13 (4H, 2s,—C(=NH$_2^+$)NH$_2$); 8.09–6.83 (15H, m, aryl-H); 5.66 (2H, s, N—CH$_2$-Phenyl); 3.18 (4H, m, —CH$_2$CH$_2$—).

EXAMPLE 2

$^1$H-NMR (250 MHz, DMSO-d6): δ=10.71; 9.41; 9.21 (5H,3s,H$^+$; —C(=NH$_2^+$)NH$_2$); 7.89–6.88 (12H,m,aryl-H); 4,09; 3.16 (4H,2m,N—CH$_2$CH$_2$—N); 3.76 (3H,s,N—CH$_3$); 3.26 (4H,m,—CH$_2$CH$_2$—); 3.15 (4H,m,N—(CH$_2$CH$_3$)$_2$; 1.16 (6H,m,N—(CH$_2$CH$_3$)$_2$).

EXAMPLE 3

$^1$H-NMR(250 MHz, DMSO-d6): δ=11.03; 9.59; 9.42 (5H, 3s, H$^+$; —C(=NH$_2^+$)NH$_2$); 8.05–6.95 (12H,m,aryl-H); 4.31; 3.06 (4H, 2m, N—CH$_2$CH$_2$—N).

EXAMPLE 4

$^1$H-NMR (250 MHz, CD$_3$OD): δ=7.70–6.49 (16H, m, aryl-H); 3.60 (3H, s, N—CH$_3$); (2H, s, N—CH$_2$—); 3.21 (4H, s, —CH$_2$—CH$_2$—); 2.79 (6H, s, N—(CH$_3$)$_2$).

EXAMPLE 5

$^1$H-NMR (250 MHz, DMSO-d6): δ=10.93; 8.57 (4H, 2s, NH$_3$; H$^+$); 7.88–6.90 (12H, m, aryl-H); 4.13; 3.15 (4H, 2m, N—CH$_2$CH$_2$N); 3.77 (3H, s, N—CH$_3$); 4.00 (2H, m, N—CH$_2$); 3.17 (4H, m, N—(CH$_2$—CH$_3$)$_2$); 1.16 (6H, m, N—(CH$_2$CH$_3$)$_2$).

EXAMPLE 6

$^1$H-NMR (250 MHz, DMSO-d6): δ=10.33; 9.33; 9.13 (5H, 3s, H$^+$; —C(=NH$_2^+$)NH$_2$); 4.13; 3.00 (4H, 2m, N—CH$_2$—CH$_2$CH$_2$N); 3.70 (3H, s, N—CH$_3$); 3.22 (4H, s, —CH$_2$—CH$_2$—; 2.97 (4H, m, N—(CH$_2$CH$_3$)$_2$; 1.72 (2H, m, N—CH$_2$—CH$_2$—CH$_2$—); 1.14 (6H, m, N—(CH$_2$CH$_3$)$_2$).

EXAMPLE 7

$^1$H-NMR (250 MHz, DMSO-d6): δ=10.25 (1H, s, H$^+$); 9.46; 9.29 (4H, 2s, —C(=NH$_2^+$)NH$_2$); 7.95–6.77 (12H, m, aryl-H); 4.24 (2H, m, CH—N-cyclohexyl); 3.78 (3H, s, N—CH$_3$); 3.27 (4H, s, —CH$_2$—CH$_2$—); 2.94–0.99 (16H, m, CH$_2$-cyclohex.; N—(CH$_2$CH$_2$CH$_3$)$_2$); 0.84 (6H, m, N—(CH$_2$CH$_2$CH$_3$)$_2$).

EXAMPLE 8

$^1$H-NMR (250 MHz, DMSO-d6): δ=11.12; 9.40; 9.20 (5H, 3s, H$^+$; —C(=NH$_2^+$)NH$_2$); 7.99–6.91 (12H, m, aryl-H); 3.85 (3H, s, N—CH$_3$); 2.48 (3H, s, N—CH$_3$-pyrrol.); 3.25 (4H, s, —CH$_2$CH$_2$—); 3.78–1.51 (9H, m, CH—/CH$_2$-pyrrol.).

EXAMPLE 9

$^1$H-NMR (250 MHz, DMSO-d6): δ=9.52; 9.35 (4H, 2s, —C(=NH$_2^+$)NH$_2$); 8.02–6.90 (12H, m, aryl-H); 3.91 (N—CH-pyrrol.); 3.79 (3H, s, N—CH$_3$); 3.23 (3H, s, N—CH$_3$-pyrrol.); 3.28–1.53 (8H, —CH$_2$-pyrrol.); 3.40 (4H, s, —CH$_2$—CH$_2$—).

EXAMPLE 10

$^1$H-NMR (250 MHz, CD$_3$OD): δ=7.76–6.83 (17H,m,aryl-H); 3.71 (3H,s,N—CH$_3$); 3.47; 3.35 (2H,m,N—CH$_2$—); 3.28 (5H,m,—CH$_2$CH$_2$—,CH-pyroll.); 2,91–1.64 (6H,m, CH$_2$-pyroll.).

EXAMPLE 11

$^1$H-NMR (250 MHz,DMSO-d6): δ=9.29; 9.09; 8.97; 8.31 (6H,m,H$^+$; —C(=NH$_2^+$)NH$_2$); 7.86–6.68 (12H,m,aryl-H); 4.51 (1H,m,CH-pip.); 3.72 (3H,s,N—CH$_3$); 3.14 (4H,s,—CH$_2$—CH$_2$); 3.32–2.87 (4H,m,N—CH$_2$-pip.); 2.00–1.34 (4H,m,CH$_2$-pip.).

EXAMPLE 12

$^1$H-NMR (250 MHz,CD$_3$OD): δ=7.95–6.87 (12H,m,aryl-H); 4.67 (1H,m,pip.CH); 3.75 (3H,s,N—CH$_3$); 3.33 (4H, s,—CH$_2$—CH$_2$—); 3.58–3.14 (4H,m,N—CH$_2$-pip.); 2.79 (3H,s,N—CH$_3$-pip.); 2.24–1.61 (4H,m,CH$_2$-pip.).

EXAMPLE 13

$^1$H-NMR (250 MHz, DMSO-d6): δ=10.40; 9.52; 9.29 (5H, 3s, H$^+$, —C(=NH$_2^+$)NH$_2$); 4.57 (1H, m, N—CH Pip.); 4.22 (2H, s, N—CH$_2$-Phenyl); 3.81 (3H, s, N—CH$_3$); 3.30 (4H, s, —CH$_2$—CH$_2$—); 3.19–1.67 (8H, m, pip.—CH$_2$—).

EXAMPLE 14

$^1$H-NMR (250 MHz,DMSO-d6): δ=7.95–7.51 (12H,m, aryl-H); 4.82 (1H,m,pyrrol.-H), 3.73 (3H,s,N—CH$_3$); 3.25 (4H,s,—CH$_2$—CH$_2$—); 3.47–1.37 (6H,m,CH$_2$-pyrrol.);

EXAMPLE 16

$^1$H-NMR (250 MHz, DMSO-d6): δ=11.03; 9.62; 9.42 (5H, 3s, H$^+$; —C(=NH$_2^+$)NH$_2$); 8.14–7.23 (12H, m, aryl-H); 4.63; 3.68 (4H, 2m, N—CH$_2$CH$_2$—O); 4.20; 3.72 (4H, 2m, N—CH$_2$CH$_2$—N); 3.81 (1H, t, J=5.5 Hz, OH); 3.64; 3.44 (4H, 2m, —CH$_2$CH$_2$—); 3.20 (4H, qu, J=7.0 Hz, N—(CH$_2$CH$_3$)$_2$; 1.20 (6H, t, J=7.0 Hz, N—(CH$_2$–CH$_3$)$_2$).

EXAMPLE 17

$^1$H-NMR (250 MHz, DMSO-d6): δ=10.08 (4H, broad, —C(=NH$_2^+$)NH$_2$); 7.79–6.82 (12H, m, aryl-H); 4.36 (2H, m, N—CH$_2$—CH$_2$—O); 3.64 (2H, m, N—CH$_2$CH$_2$O—); 3.60; 2.42 (4H, 2m, N—CH$_2$CH$_2$—N); 3.22 (4H, s, —CH$_2$—); 3.17 (3H, s, OCH$_3$); 2.38 (4H, qu, J=7.0 Hz, N—(CH$_2$—CH$_3$)$_2$); 0.83 (6H, t, J=7.0 Hz, N—(CH$_2$—CH$_3$)$_2$).

EXAMPLE 18

$^1$H-NMR (250 MHz, DMSO-d6): δ=10.64; 9.49; 9.26 (5H,3s,H$^+$; —C(=NH$_2^+$)NH$_2$); 7.95–6.91 (12H,m,aryl-H); 4.20 (2H,m,N—CH$_2$—); 3.29 (4H,m,—CH$_2$CH$_2$—); 3.14 (4H,m,N—(CH$_2$CH$_3$)$_2$; 1.70 (2H,m,N—CH$_2$CH$_2$—CH$_3$); 1.16 (6H,m,N—(CH$_2$CH$_3$).

EXAMPLE 19

$^1$H-NMR (250 MHz, DMSO-d6): δ=10.94; 9.58; 9.36 (5H, 3s, H$^+$; —C(=NH$_2^+$)NH$_2$); 8.14–7.20 (12H, m aryl-H); 4.54 (2H, m, N—CH$_2$); 4.18; 3.62 (4H, 2m, N—CH$_2$CH$_2$—$_N$); 3.60 (2H, m, OCH$_2$); 3.42 (4H, m, —CH$_2$CH$_2$—); 3.20 (4H, m, N(—CH$_2$CH$_3$)$_2$; 1.94 (2H, m, N—CH$_2$CH$_2$CH$_2$—O); 1.21 (6H, m, N-(CH$_2$CH$_3$)$_2$). OH in the solvent blind peak.

EXAMPLE 24

$^1$H-NMR (250 MHz, DMSO-d6): δ=9.73; 9.54 (4H, 2s, —C(=NH$_2^+$)NH$_2$); 8.14–7.04 (17H, m, aryl-H); 4.62; 3.15 (4H, 2m, N—CH$_2$CH$_2$-Phenyl); 4.10; 3.02 (4H, 2m, N—CH$_2$CH$_2$—N); 3.28; 3.06 (4H, 2m, —CH$_2$CH$_2$—); 2.99 (4H, m, N—(CH$_2$CH$_3$)$_2$; 1.15 (6H, m, N—(CH$_2$CH$_3$)$_2$).

EXAMPLE 25

$^1$H-NMR (250 MHz,DMSO-d6); δ=10.81; 9.47; 9.30 (5H,3s,H$^+$; —C(=NH$_2^+$)NH$_2$); 7.97–6.89 (7H,m,aryl-H); 4,23 (2H,m,N—CH$_2$CH$_2$CH$_2$—); 4.10; 3.16 (4H,2m,N—CH$_2$CH$_2$—N); 3.19 (4H,m,N—(CH$_2$CH$_3$)$_2$); 3.18 (4H,m,—CH$_2$—CH$_2$—); 2.67 (2H,m,xx—CH$_2$—); 1,99 (2,m,xx-CH$_2$CH$_2$—); 1.14 (6H,m,N—(CH$_2$CH$_3$)$_2$.

EXAMPLE 26

$^1$H-NMR (250 MHz, DMSO-d6): δ=10.26 (4H, broad, —C(=NH$_2^+$)NH$_2$); 7.92–6.80 (16H, m, aryl-H); 4.68 (2H, m, N—CH$_2$—CH$_2$O—); 4.28; 2.11 (4H, 2m, N—CH$_2$CH$_2$—N); 3.69 (2H, m, N—CH$_2$CH$_2$O); 3.58 (3H, s, OCH$_3$); 3.38 (4H, m, —CH$_2$—CH$_2$—); 2.05 (4H, qu, J≦7.0 Hz, N—(CH$_2$CH$_3$)$_2$); 0.83 (6H, t, J=7.0 Hz, N—(CH$_2$—CH$_3$)$_2$).

EXAMPLE 27

$^1$H-NMR(250 MHz, DMSO-d6): δ=10.30(4H,s, —C(=NH$_2^+$)NH$_2$); 7.92–6.89(12H,m,aryl-H); 4.46–3.53 (13H,m,N—CH$_2$CH$_2$—N; N.CH$_2$—CH—O—CH$_2$—; —CH$_2$—CH$_2$—); 2.45(4H, qu, J=7.0 Hz, N—(CH$_2$CH$_3$)$_2$); 1.84–1.44(4H,m, CH$_2$-THF); 0.86 (6H,t,J=7.Hz, N—(CH$_2$CH$_3$)$_2$).

EXAMPLE 28

$^1$H-NMR (250 MHz, DMSO-d6): δ=10.87; 9.45; 9.27 (5H, 3s, H$^+$; —C(=NH$_2^+$)NH$_2$); 8.41–6.89 (14H, m, aryl-H); 4.19; 3.12 (4H, 2m, N—CH$_2$CH$_2$—N); 3.73 (3H, S, N—CH$_3$); 3.24 (4H, S, —CH$_2$—CH$_2$—); 3.11 (4H, m, N—(CH$_2$CH$_3$)$_2$); 1.10 (6H, m, N—(CH$_2$CH$_3$)$_2$).

EXAMPLE 31

$^1$H-NMR (250 MHz, DMSO-d6): δ=7.80–6.79 (12H, m, aryl-H); 3.74 (3H, s, N—CH$_3$); 3.67; 2.46 (4H, 2m, N—CH$_2$CH$_2$—N); 3.21 (4H, s, —CH$_2$CH$_2$—); 2.48 (4H, m, N(—CH$_2$—CH$_2$—)$_2$ cyclohept.); 1.82 (4H, m, N—(CH$_2$CH$_2$)$_2$ cyclohept.); 1.30 (4H, N—(CH$_2$CH$_2$CH$_2$) cyclohept).

EXAMPLE 33

$^1$H-NMR (250 MHz, DMSO-d6): δ=7.92–6.88 (12H, m, aryl-H); 3.76 (3H, s, M-CH$_3$); 3.74; 2.27 (4H, m, N—CH$_2$CH$_2$-M); 3.24 (4H, s, —CH$_2$CH$_2$—); 2.24; 1.53–1.17 (10H, 2m, piper.H);

EXAMPLE 34

$^1$H-NMR (250 MHz, DMSO-d6): δ=7.77–6.76 (12H, m, aryl-H); 3.71 (3H, s, N—CH$_3$); 3.68; 2.38 (4H, 2m, N—CH$_2$CH$_2$-M); 3.79 (4H, s, —CH$_2$—CH$_2$—); 2.35; 1.61 (8H, 2m, CH-pyrrol.);

EXAMPLE 56

$^1$H-NMR (250 MHz, CH$_3$OD): δ=7.91–7.26 (12H, m, aryl-H); 4.23; 3.38 (4H, 2m, N—CH$_2$—CH$_2$—N); 3.96 (3H, s, N—CH$_3$); 3.58; 3.38 (4H, 2m, —CH$_2$CH$_2$—); 4.00; 3.36 (8H, 2m, CH$_3$-morpholine).

EXAMPLE 59

$^1$H-NMR (250MHz, CD$_3$OD):δ=7.83–7.05(12H,m,aryl-H); 4.23–3.79 (5H,m,N—CH$_2$—CH—OXX)3.89;2.75(4H, 2m, N—CH$_2$CH$_2$—N); 3.34(4H,M,—CH$_2$CH$_2$—); 2.68 (4H, qu,J=7.0 Hz; N(CH$_2$CH$_3$,); 2.25–1.63 (4H,m, CH$_2$-THF); 1.10 (6H,t,J=7.0 Hz, N—(CH$_2$CH$_3$)$_2$).

EXAMPLE 60

$^1$H-NMR (250 MHz, DMSO-d6): δ=9.57 (1H, s, =N—OH); 7.77–6.86 (12H, m, aryl-H); 5.78 (2H, s, NH$_2$); 4.98 (1H, t, J=5.5 Hz, OH); 4.23; 3.67 (4H, 2m, N—CH$_2$CH$_2$—O); 3.67; 2.42 (4H, 2m, N—CH$_2$CH$_2$N); 3.15 (4H, m, —CH$_2$—CH$_2$—); 2.40 (4H, qu, J=7.0 Hz, N—(CH$_2$CH$_3$)$_2$); 0.84 (6H, t, J=7.0 Hz, N—(CH$_2$CH$_3$)$_2$).

EXAMPLE 61

$^1$H-NMR(250 MHz, DMSO-d6): δ=9.70 (H, s, OH); 7.90–6.93 (12H, m, aryl-H); 5.85 (2H,s,NH$_2$); 4.42 (2H,m, N—CH$_2$—CH$_2$—O); 3.70 (2H, m, N—CH$_2$—CH$_3$—O); 3.63; 2.46 (4H, m,N—CH$_2$CH$_2$—N); 3.36 (3H, s, OCH$_3$); 3.20 (4H,s, —CH$_2$CH$_2$—); 2.43 (4H, qu, J=7.0 Hz; N—(CH$_2$CH$_3$)$_2$; 0.85(6H, t, J=7.0 Hz, N—(CH$_2$CH$_3$)$_2$).

EXAMPLE 62

$^1$H-NMR (250 MHz, DMSO-d6): δ=9.72 (1H, s, c=N—OH); 7.91–6.96 (12H, m, aryl-H); 5.86 (2H, s, NH$_2$); 4.79 (1H, t, J=5.5Hz, OH); 4.28 (2H, m, N—CH$_2$CH$_2$CH$_2$);3.71; 2.47 (4H, 2m, N—CH$_2$CH$_2$—N); 3.40 (2H, m, OCH$_2$); 3.21 (4H, s, —CH$_2$—CH$_2$—); 2.43 (4H, qu, J=7.0 Hz, N—(CH$_2$CH$_3$)$_2$); 1.83 (2H, m, N—CH$_2$CH$_2$CH$_2$); 0.85 (6H, t, J=7.0 Hz, N—(CH$_2$CH$_3$)$_2$).

EXAMPLE 63

$^1$H-NMR (250 MHz, DMSO-d6): δ=9.70 (1H, s, OH); 7.84–6.84 (16H, m, aryl-H); 5.86 (2H, s, NH$_2$); 4.68 (2H, m, N—CH$_2$—CH$_2$—O); 4.28; 2.48 (4H, 2m, N—CH$_2$CH$_2$—N); 3.72 (2H, m, N—CH$_2$—CH$_2$—O); 3.60 (3H, s, OCH$_3$); 3.38; 3.24 (4H, 2m, —CH$_2$—CH$_2$—); 2.48 (4H, m, N(—CH$_2$CH$_3$)$_2$; 0.85 (6H, m, N—(CH$_2$CH$_3$)$_2$).

The compounds according to the invention are characterised by their tryptase-inhibiting activity. This ability to inhibit tryptase was investigated using the test described below. The measurement is carried out in Tris HCl buffer (100 mM), which additionally contains calcium (5 mM) and heparin (100 mg/ml), at pH 7.4. The standard used is rh beta tryptase which may be obtained commercially from Promega, for example. The substrate used is N-p-tosyl-Gly-Pro-Lys-para-nitroaniline in a concentration of 0.6 mM. The substrate is digested with tryptase to form p-nitroaniline which can be measured at 405 nm. Usually, an incubation period of 5 minutes and an incubation temperature of 37° C. are chosen. The enzyme activity used is 0.91 U/ml. The measurements are carried out in an Autoanalyser (CobasBio) made by Hofmann LaRoche. The potential inhibitory substances are used in concentrations of 10 μM in the screening, the inhibition of the tryptase being given in percent. The IC$_{50}$ is determined at over 70% inhibition (concentration at which 50% of the enzyme activity is inhibited). After 5 minutes' pre-incubation of the potential inhibitory substances, the substrate is added to start the reaction, the formation of p-nitroaniline being taken as a measurement of the enzyme activity after 5 minutes, after testing the linearity.

The data obtained after the above test has been carried out (IC50 values) can be found in Table 3.

TABLE 3

| Example | IC$_{50}$ [μM] |
|---|---|
| 2 | 0.025 |
| 3 | 0.132 |
| 4 | 0.123 |
| 5 | 0.1 |
| 6 | 0.047 |
| 7 | 0.109 |
| 8 | 0.089 |
| 9 | 0.062 |
| 10 | 0.068 |
| 11 | 0.09 |
| 12 | 0.179 |
| 13 | 0.076 |
| 14 | 0.082 |
| 16 | 0.121 |
| 17 | 0.062 |
| 18 | 0.292 |
| 19 | 0.239 |
| 24 | 0.19 |
| 25 | 0.412 |
| 26 | 0.074 |
| 27 | 0.273 |
| 28 | 0.027 |
| 31 | 0.031 |
| 33 | 0.044 |
| 34 | 0.043 |
| 35 | 0.0066 |
| 43 | 0.025 |
| 44 | 0.022 |
| 45 | 0.022 |
| 46 | 0.03 |
| 47 | 0.0703 |
| 48 | 0.1438 |
| 49 | 0.186 |
| 50 | 0.215 |
| 51 | 0.035 |
| 52 | 0.029 |
| 53 | 0.038 |
| 54 | 0.027 |
| 55 | 0.028 |

The tryptase inhibitors according to the invention may be administered orally, transdermally, by inhalation or parenterally. The compounds according to the invention occur as active ingredients in conventional preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal systems etc. An effective dose of the compounds according to the invention is between 1 and 100, preferably between 1 and 50, most preferably between 5–30 mg/dose for oral administration, and between 0.001 and 50, preferably between 0.1 and 10 mg/dose for intravenous or intramuscular administration. For inhalation, according to the invention, solutions containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10–300 mg per adult.

The Examples which follow illustrate the present invention without restricting its scope:

EXAMPLES OF PHARMACEUTICAL FORMULATIONS

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The solid fat is melted. The ground active substance is homogeneously dispersed at 40° C. It is cooled to 38° C. and poured into slightly chilled suppository moulds.

What is claimed is:

1. A compound of the formula (I)

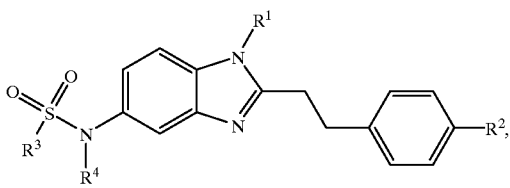

(I)

wherein:

$R^1$ is:
(a) $C_1$–$C_6$-alkyl, $C_2$–$C_6$-alkenyl or $C_2$–$C_6$-alkynyl, each of which is unsubstituted or mono-, di- or trisubstituted by one or more substituents selected from the group consisting of hydroxy, $C_1$–$C_4$-alkoxy, $CF_3$, phenoxy, COOH, halogen, —CO($C_1$–$C_4$-alkoxy), —$CONH_2$, —CO—NH($C_1$–$C_4$-alkyl), —CO—N($C_1$–$C_4$-alkyl)$_2$, —$NH_2$, —NH($C_1$–$C_4$-alkyl), —N($C_1$–$C_4$-alkyl)$_2$ and $C_1$–$C_4$-alkoxy-phenoxy, (b) $C_3$–$C_8$-cycloalkyl optionally linked via a $C_1$–$C_4$-alkylene bridge, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, (c) phenyl-$C_1$–$C_4$-alkyl, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, or (d) a 5- or 6-membered, saturated or unsaturated heterocyclic group linked directly or via a $C_1$–$C_4$-alkylene bridge, which contains one or two hetero atoms selected from the group consisting of oxygen, nitrogen or sulphur and which is unsubstituted or substituted by $C_1$–$C_4$-alkyl or benzyl;

$R^2$ is —C(=NH)$NH_2$ or —$CH_2$—$NH_2$;

$R^3$ is phenyl, benzyl, naphthyl, furanyl, benzofuranyl, quinolyl, isoquinolyl, thienyl or benzothienyl; and, $R^4$ is:
(a) $C_1$–$C_6$-alkyl group, which is mono- or disubstituted by one or two substituents selected from the group consisting of —$NH_2$, —NH($C_1$–$C_4$-alkyl), —N($C_1$–$C_4$-alkyl)$_2$, —C(=NH)$NH_2$ and —NH—C(=NH)$NH_2$, (b) a 5-, 6- or 7-membered, saturated or unsaturated heterocyclic group linked directly or via a $C_1$–$C_4$-alkylene bridge or via a $C_1$–$C_4$-alkylene-CO bridge which contains one, two or three hetero atoms selected from the group consisting of oxygen, nitrogen and sulphur and which is unsubstituted or substituted by $C_1$–$C_4$-alkyl, $C_1$–$C_4$-hydroxyalkyl, benzyl or pyridyl, (c) $C_3$–$C_8$-cycloalkyl, which is unsubstituted or mono- or disubstituted by one or two substituents selected from the group consisting of —$NH_2$, —NH($C_1$–$C_4$-alkyl), —N($C_1$–$C_4$-alkyl)$_2$, —C(=NH)$NH_2$ and —NH—C(=NH)$NH_2$, (d) phenyl, benzyl or phenylethyl, each of which is unsubstituted or mono- or disubstituted at the phenyl ring by one or two substituents selected from the group consisting of —$NH_2$, —NH($C_1$–$C_4$-alkyl), —N($C_1$–$C_4$-alkyl)$_2$, —$C_1$–$C_4$-alkyl-$NH_2$, —C(=NH)$NH_2$ and —NH—C(=NH)$NH_2$;

or a tautomer or pharmaceutically acceptable salt thereof.

2. A compound of the formula (I), according to claim 1, wherein:

$R^1$ is:
(a) $C_1$–$C_5$-alkyl, which is unsubstituted or mono-, di- or trisubstituted by one or more substituents selected from the group consisting of hydroxy, $C_1$–$C_4$-alkoxy, $CF_3$, phenoxy, COOH, —CO($C_1$–$C_4$-alkoxy), —$CONH_2$, —CO—NH($C_1$–$C_4$-alkyl), —CO—N ($C_1$–$C_4$-alkyl)$_2$ and $C_1$–$C_4$-alkoxy-phenoxy, (b) $C_3$–$C_8$-cycloalkyl optionally linked via a $C_1$–$C_4$-alkylene bridge, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, (c) phenyl-$C_1$–$C_4$-alkyl, which is unsubstituted or mono-, di- or trisubstituted by one or more substituents selected from the group consisting of hydroxy, $C_1$–$C_4$-alkoxy, carboxy, $C_1$–$C_4$-alkoxycarbonyl and $CF_3$, or (d) a 5- or 6-membered, saturated or unsaturated heterocyclic group linked directly or via a $C_1$–$C_4$-alkylene bridge, which contains one or two hetero atoms selected from the group consisting of oxygen, nitrogen and sulphur and which is unsubstituted or substituted by $C_1$–$C_4$-alkyl or benzyl;

$R^2$ is —C(=NH)$NH_2$ or —$CH_2$—$NH_2$;

$R^3$ is phenyl, benzyl, quinolyl, benzothienyl or naphthyl; and, $R^4$ is:
(a) $C_1$–$C_6$-alkyl group, which is mono- or disubstituted by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$,
(b) a 5-, 6- or 7-membered, saturated or unsaturated nitrogen-containing heterocyclic group linked directly or via a $C_1$–$C_4$-alkylene bridge or via a $C_1$–$C_4$-alkylene-CO bridge, which optionally contains one or two additional hetero atoms selected from the group consisting of oxygen, nitrogen and sulphur and which is unsubstituted or substituted by $C_1$–$C_4$-alkyl, $C_1$–$C_4$-hydroxyalkyl, benzyl or pyridyl;
(c) cyclopropyl, cyclopentyl or cyclohexyl, each of which is mono- or disubstituted by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$, or
(d) phenyl, benzyl or phenylethyl, each of which is mono- or disubstituted at the phenyl ring by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$;

or a tautomer or pharmaceutically acceptable salt thereof.

3. A compound of the formula 1, according to claim 1, wherein:

$R^1$ is:
(a) methyl, ethyl, propyl, butyl or pentyl, each of which is unsubstituted or substituted by hydroxy, methoxy, ethoxy, propoxy, $CF_3$, phenoxy, COOH, $CONH_2$, CONHMe or methoxy-phenoxy,
(b) benzyl, phenylethyl or phenylpropyl, each of which is unsubstituted or mono- or disubstituted at the phenyl ring by one or two substituents selected from the group consisting of hydroxy, methoxy, ethoxy, carboxy, methoxycarbonyl, ethoxycarbonyl and $CF_3$,
(c) a 5- or 6-membered, saturated or unsaturated heterocyclic group linked directly or via a $C_1$–$C_4$-alkylene bridge, which contains one or two hetero atoms selected from the group consisting of oxygen and nitrogen and is unsubstituted or substituted by methyl, ethyl, propyl or benzyl;

$R^2$ is —C(=NH)$NH_2$ or —$CH_2$—$NH_2$;

$R^3$ is phenyl, benzyl, quinolyl, benzothienyl or naphthyl; and, $R^4$ is:
(a) ethyl, propyl, butyl, pentyl or hexyl, each of which is mono- or disubstituted by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$,
(b) a 5-, 6- or 7-membered, saturated or unsaturated nitrogen-containing heterocyclic group linked directly or via a $C_1$–$C_4$-alkylene bridge or via a $C_1$–$C_3$-alkylene-CO bridge, which optionally contains one or two additional hetero atoms selected from the group consisting of oxygen and nitrogen and which is unsubstituted or substituted by methyl, ethyl, propyl, 3-hydroxypropyl or benzyl,
(c) cyclopentyl or cyclohexyl, each of which is mono- or disubstituted by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$, or
(d) benzyl or phenylethyl, each of which is mono- or disubstituted at the phenyl ring by one or two substituents selected from the group consisting of —$NH_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)$NH_2$ and —NH—C(=NH)$NH_2$;

or a tautomer or pharmaceutically acceptable salt thereof.

4. A compound of the formula I, according to claim 1, wherein:

$R^1$ is:
(a) methyl, ethyl (which is unsubstituted or substituted by hydroxy, methoxy, ethoxy, phenoxy or methoxy-phenoxy), propyl (which is unsubstituted or substituted by hydroxy, methoxy or ethoxy), butyl or pentyl,
(b) benzyl which is unsubstituted or mono- or disubstituted at the phenyl ring by one or two substituents selected from the group consisting of hydroxy, carboxy, methoxycarbonyl, ethoxycarbonyl, methoxy, ethoxy or $CF_3$, or phenylethyl or phenylpropyl, or
(c) a 5- or 6-membered, saturated or unsaturated heterocyclic group linked directly or via a methylene or ethylene bridge which contains oxygen or nitrogen as the heteroatom and which is unsubstituted or substituted by methyl, ethyl, propyl or benzyl;

$R^2$ is —C(=NH)$NH_2$ or —$CH_2$—$NH_2$;

$R^3$ is phenyl, benzyl, quinolyl, isoquinolyl, benzothienyl or naphthyl,; and, $R^4$ is:
(a) ethyl or propyl, each of which is substituted by —$NH_2$, —N(methyl)$_2$, —N(ethyl)$_2$, —N(n-propyl)$_2$ or —C(=NH)$NH_2$,
(b) a 5-, 6- or 7-membered, saturated or unsaturated nitrogen-containing heterocyclic group linked directly or via a methylene or ethylene bridge, which optionally contains an oxygen as a further heteroatom and which is unsubstituted or substituted by methyl, ethyl, propyl, 3-hydroxypropyl or benzyl,
(c) cyclopentyl or cyclohexyl, each of which is substituted by —$NH_2$, —N(methyl)$_2$, —N(ethyl)$_2$, —N(n-propyl)$_2$ or —C(=NH)$NH_2$, or
(d) benzyl which is substituted at the phenyl ring by —$NH_2$, —N(methyl)$_2$, —N(ethyl)$_2$, —N(n-propyl)$_2$ or —C(=NH)$NH_2$, or a tautomer or pharmaceutically acceptable salt thereof.

5. A compound of the formula I, according to claim 1, wherein:

$R^1$ is:
(a) methyl, ethyl, hydroxyethyl, methoxyethyl, methoxy-phenoxy-ethyl, propyl, hydroxypropyl, ethoxypropyl, or pentyl, or (b) benzyl, which is mono- or disubstituted at the phenyl ring by one or two substituents selected from the group consisting of carboxy, ethoxycarbonyl, or $CF_3$,;

$R^2$ is —C(=NH)$NH_2$ or —$CH_2$—$NH_2$;

$R^3$ is phenyl, benzyl, quinolyl, benzothienyl or naphthyl; and, $R^4$ is:
(a) diethylaminoethyl or diethylaminopropyl,
(b) a pyridine, pyrimidine, pyrrolidine, morpholine, azepine or piperidine linked directly or via a methylene or methylcarbonyl bridge, each of which is unsubstituted or substituted by methyl, 3-hydroxypropyl or benzyl, or cyclohexyl substituted by —N(n-propyl)$_2$, or
(c) benzyl which is substituted at the phenyl ring by —N(methyl)$_2$ or —C(=NH)$NH_2$;

or a tautomer or pharmaceutically acceptable salt thereof.

6. A compound of the formula I, according to claim 1, wherein:

$R^1$ is methyl, hydroxyethyl, methoxyethyl, methoxyphenoxy-ethyl, propyl, hydroxypropyl, ethoxypropyl, phenylethyl, phenylpropyl or a tetrahydrofuranyl linked via a methylene bridge;

$R^2$ is —C(=NH)$NH_2$ or —$CH_2$—$NH_2$;

$R^3$ is phenyl, benzyl, quinol-8-yl, benzo[b]thien-3-yl or naphthyl; and, $R^4$ is:
(a) diethylaminoethyl or diethylaminopropyl,
(b) pyridine linked directly or via a methylene or ethylene bridge, which is unsubstituted or substituted by methyl or benzyl,
(c) pyrrolidine linked directly or via a methylene or ethylene bridge, which is unsubstituted or substituted by methyl or benzyl,
(d) piperidine linked directly or via a methylene or ethylene bridge which is unsubstituted or substituted by methyl or benzyl,
(e) morpholine linked directly or via a methylene or ethylene bridge,
(f) azepine linked directly or via a methylene or ethylene bridge,
(g) cyclohexyl substituted by —N(n-propyl)$_2$, or
(h) benzyl substituted at the phenyl ring by —N(methyl)$_2$;

or a tautomer or pharmaceutically acceptable salt thereof.

7. A compound of the formula II, wherein:

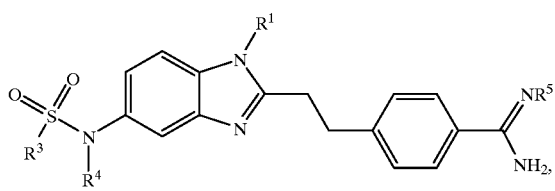

(II)

wherein $R^1$ is:
(a) $C_1$–$C_6$-alkyl, $C_2$–$C_6$-alkenyl or $C_2$–$C_6$-alkynyl, each of which is unsubstituted or mono-, di- or trisubstituted by one or more substituents selected from the group consisting of hydroxy, $C_1$–$C_4$-alkoxy, $CF_3$, phenoxy, COOH, halogen, —CO($C_1$–$C_4$-alkoxy), —$CONH_2$, —CO—NH($C_1$–$C_4$-alkyl), —CO—N($C_1$–$C_4$-alkyl)$_2$, —$NH_2$, —NH($C_1$–$C_4$-alkyl), —N($C_1$–$C_4$-alkyl)$_2$ and $C_1$–$C_4$-alkoxyphenoxy, (b) $C_3$–$C_8$-cycloalkyl optionally linked via a $C_1$–$C_4$-alkylene bridge, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, (c) phenyl-$C_1$–$C_4$-alkyl, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, or (d) a 5- or 6-membered, saturated or unsaturated heterocyclic group linked directly or via a $C_1$–$C_4$-alkylene bridge, which contains one or two hetero atoms selected from the group consisting of oxygen, nitrogen and sulphur and which is unsubstituted or substituted by $C_1$–$C_4$-alkyl or benzyl;

$R^3$ is phenyl, benzyl, naphthyl, furanyl, benzofuranyl, quinolyl, isoquinolyl, thienyl or benzothienyl, or $R^3$ is $C_1$–$C_4$-alkyl which is substituted by —C(=NOH)$NH_2$, —C(=NCOO—$C_1$–$C_{12}$-alkyl)$NH_2$ or —C(=NCOO—$C_1$–$C_8$-alkyl-phenyl)$NH_2$;

$R^4$ is:
(a) $C_1$–$C_6$-alkyl, which is unsubstituted or mono- or disubstituted by one or two substituents selected from the group consisting of —$NH_2$, —NH($C_1$–$C_4$-alkyl), —N($C_1$–$C_4$-alkyl)$_2$, —C(=NH)$NH_2$ and —NH—C(=NH)$NH_2$, (b) a 5-, 6- or 7-membered, saturated or unsaturated heterocyclic group linked directly or via a $C_1$–$C_4$-alkylene bridge or via a $C_1$–$C_4$-alkylene-CO bridge which contains one, two or three hetero atoms selected from the group consisting of oxygen, nitrogen and sulphur and which is unsubstituted or substituted by $C_1$–$C_4$-alkyl, $C_1$–$C_4$-hydroxyalkyl, benzyl or pyridyl, (c) $C_3$–$C_8$-cycloalkyl, which is unsubstituted or mono- or disubstituted by one or two substituents selected from the group consisting of —$NH_2$, —NH($C_1$–$C_4$-alkyl), —N($C_1$–$C_4$-alkyl)$_2$, —C(=NH)$NH_2$ and —NH—C(=NH)$NH_2$, or (d) phenyl, benzyl or phenylethyl, each of which is unsubstituted or mono- or disubstituted at the phenyl ring by one or two substituents selected from the group consisting of —$NH_2$, —NH($C_1$–$C_4$-alkyl), —N($C_1$–$C_4$-alkyl)$_2$, —$C_{1-4}$-alkyl-$NH_2$, —C(=NH)$NH_2$ and —NH—C(=NH)$NH_2$; and, $R^5$ is hydroxy, —COO—$C_1$–$C_{12}$-alkyl, —CO-phenyl, —CO-pyridyl or —COO—$C_1$–$C_8$-alkyl-phenyl, whilst in the group $R^5$ the phenyl ring may be substituted in each case by $C_1$–$C_4$-alkyl, $C_1$–$C_4$-alkoxy, OH, halogen or $CF_3$;

or a tautomer or pharmaceutically acceptable salt thereof.

8. A compound of the formula II, according to claim 7, wherein:

$R^3$ is phenyl, benzyl, naphthyl, furanyl, benzofuranyl, quinolyl, isoquinolyl, thienyl or benzothienyl, or $R^3$ is $C_1$–$C_4$-alkyl which is substituted by —C(=NOH)$NH_2$, —C(=NCOO—$C_1$–$C_6$-alkyl)$NH_2$ or —C(=NCOO—$C_1$–$C_6$-alkyl-phenyl)$NH_2$; and, $R^5$ is hydroxy, —COO—$C_1$–$C_6$-alkyl, —CO-phenyl, —CO-pyridyl or —COO—$C_1$–$C_6$-alkyl-phenyl, whilst in the group $R^5$ the phenyl ring may be substituted in each case by $C_1$–$C_4$-alkyl, $C_1$–$C_4$-alkoxy, OH, halogen or $CF_3$;

or a tautomer or pharmaceutically acceptable salt thereof.

9. A compound of the formula II, according to claim 7, wherein:

$R^5$ is hydroxy, methoxycarbonyl, ethoxycarbonyl, propyloxycarbonyl, butyloxycarbonyl, benzoyl, benzyloxycarbonyl or nicotinoyl, or a tautomer of pharmaceutically acceptable salt thereof.

10. A compound of the formula III

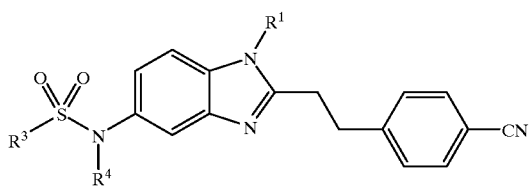

(III)

wherein:

$R^1$ is:
- (a) $C_1$–$C_6$-alkyl, $C_2$–$C_6$-alkenyl or $C_2$–$C_6$-alkynyl, each of which is unsubstituted or mono-, di- or trisubstituted by one or more substituents selected from the group consisting of hydroxy, $C_1$–$C_4$-alkoxy, $CF_3$, phenoxy, COOH, halogen, —CO($C_1$–$C_4$-alkoxy), —CONH$_2$, —CO—NH($C_1$–$C_4$-alkyl), —CO—N($C_1$–$C_4$-alkyl)$_2$, —NH$_2$, —NH($C_1$–$C_4$-alkyl), —N($C_1$–$C_4$-alkyl)$_2$ and $C_1$–$C_4$-alkoxy-phenoxy,
- (b) $C_3$–$C_8$-cycloalkyl optionally linked via a $C_1$–$C_4$-alkylene bridge, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$,
- (c) phenyl-$C_1$–$C_4$-alkyl, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$, or
- (d) a 5- or 6-membered, saturated or unsaturated heterocyclic group linked directly or via a $C_1$–$C_4$-alkylene bridge, which contains one or two hetero atoms selected from the group consisting of oxygen, nitrogen or sulphur and which is unsubstituted or substituted by $C_1$–$C_4$-alkyl or benzyl;

$R^2$ is —C(=NH)NH$_2$ or —CH$_2$—NH$_2$;

$R^3$ is phenyl, benzyl, naphthyl, furanyl, benzofuranyl, quinolyl, isoquinolyl, thienyl or benzothienyl; and, $R^4$ is:
- (a) $C_1$–$C_6$-alkyl group, which is mono- or disubstituted by one or two substituents selected from the group consisting of —NH$_2$, —NH($C_1$–$C_4$-alkyl), —N($C_1$–$C_4$-alkyl)$_2$, —C(=NH)NH$_2$ and —NH—C(=NH)NH$_2$,
- (b) a 5-, 6- or 7-membered, saturated or unsaturated heterocyclic group linked directly or via a $C_1$–$C_4$-alkylene bridge or via a $C_1$–$C_4$-alkylene-CO bridge which contains one, two or three hetero atoms selected from the group consisting of oxygen, nitrogen and sulphur and which is unsubstituted or substituted by $C_1$–$C_4$-alkyl, $C_1$–$C_4$-hydroxyalkyl, benzyl or pyridyl,
- (c) $C_3$–$C_8$-cycloalkyl, which is unsubstituted or mono- or disubstituted by one or two substituents selected from the group consisting of —NH$_2$, —NH($C_1$–$C_4$-alkyl), —N($C_1$–$C_4$-alkyl)$_2$, —C(=NH)NH$_2$ and —NH—C(=NH)NH$_2$,
- (d) phenyl, benzyl or phenylethyl, each of which is unsubstituted or mono- or disubstituted at the phenyl ring by one or two substituents selected from the group consisting of —NH$_2$, —NH($C_1$–$C_4$-alkyl), —N($C_1$–$C_4$-alkyl)$_2$, —$C_1$–$C_4$-alkyl—NH$_2$, —C(=NH)NH$_2$ and —NH—C(=NH)NH$_2$.

11. A method for treating an inflammatory or allergic disease which comprises adminstering to a host in need of such treatment a therapeutic amount of a compound of the formula I, in accordance with claim 1, 2, 3, 4, 5 or 6 or a compound of the formula II, in accordance with claim 7, 8 or 9.

12. A pharmaceutical composition comprising a compound of the formula I, in accordance with claim 1, 2, 3, 4, 5 or 6 or a compound of the formula II, in accordance with claim 7, 8 or 9, and a pharmaceutically acceptable carrier.

13. A compound of the formula (III), according to claim 10, wherein:

$R^1$ is:
- (a) $C_1$–$C_5$-alkyl, which is unsubstituted or mono-, di- or trisubstituted by one or more substituents selected from the group consisting of hydroxy, $C_1$–$C_4$-alkoxy, $CF_3$, phenoxy, COOH, —CO($C_1$–$C_4$-alkoxy), —CONH$_2$, —CO—NH($C_1$–$C_4$-alkyl) —CO—N($C_1$–$C_4$-alkyl)$_2$ and $C_1$–$C_4$-alkoxy-phenoxy,
- (b) $C_3$–$C_8$-cycloalkyl optionally linked via a $C_1$–$C_4$-alkylene bridge, which is unsubstituted or mono-, di- or trisubstituted by one or more substituents selected from the group consisting of hydroxy, $C_1$–$C_4$-alkoxy, carboxy, halogen, $C_1$–$C_4$-alkoxycarbonyl and $CF_3$,
- (c) phenyl-$C_1$–$C_4$-alkyl, which is unsubstituted or mono-, di-, or trisubstituted by one or more substituents selected from the group consisting of hydroxy, $C_1$–$C_4$-alkoxy, carboxy, $C_1$–$C_4$-alkoxycarbonyl and $CF_3$, or
- (d) a 5- or 6- membered, saturated or unsaturated heterocyclic group linked directly or via a $C_1$–$C_4$-alkylene bridge, which contains one or two hetero atoms selected from the group consisting of oxygen, nitrogen and sulphur and which is unsubstituted or substituted by $C_1$–$C_4$-alkyl or benzyl;

$R^2$ is —C(=NH)NH$_2$ or —CH$_2$–NH$_2$;

$R^3$ is phenyl, benzyl, quinolyl, benzothienyl or naphthyl; and $R^4$ is:
- (a) $C_1$–$C_6$- alkyl group, which is mono- or disubstituted by one or two substituents selected from the group consisting of —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ and —NH-C(=NH)NH$_2$,
- (b) a 5- or 6- or 7-membered, saturated or unsaturated nitrogen-containing heterocyclic group linked directly or via a $C_1$–$C_4$-alkylene bridge or via a $C_1$–$C_4$-alkylene—CO bridge, which optionally contains one or two additional hetero atoms selected from the group consisting of oxygen, nitrogen and sulphur and which is unsubstituted or substituted by $C_1$–$C_4$-alkyl, $C_1$–$C_4$ -hydroxyalkyl, benzyl or pyridyl;
- (c) cyclopropyl, cyclopentyl or cyclohexyl, each of which is mono- or disubstituted by one or two substituents selected from the group consisting of —NH$_2$, NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ and —NH—C(=NH)NH$_2$, or (d) phenyl, benzyl, or phenylethyl, each of which is mono- or disubstituted at the phenyl ring by one or two substituents selected from the group consisting of —NH$_2$, —NHmethyl, —N(methyl)$_2$, —NHethyl, —N(ethyl)$_2$, —NH(n-propyl) —N(n-propyl)$_2$, —NH(iso-propyl), —N(iso-propyl)$_2$, —C(=NH)NH$_2$ and —NH—C(=NH)NH$_2$;

or a tautomer or pharmaceutically acceptable salt thereof.

14. A compound of the formula III, according to claim 10, wherein:

$R^1$ is:

methyl, ethyl, propyl, butyl, or pentyl, each of which is unsubstituted or substituted by hydroxy, methoxy ethoxy, propoxy, CF$_3$, phenoxy, COOH, CONH$_2$, CONHMe or methoxy-phenoxy, (b) benzyl, phenylethyl or phenylpropyl, each of which is unsubstituted or mono- or disubstituted at the phenyl ring by one or two substituents selected from the group consisting of hydroxy, methoxy, ethoxy, carboxy, methoxycarbonyl, ethoxycarbonyl and CF$_3$, (c) a 5- or 6-membered, saturated or unsaturated heterocyclic group linked directly or via a C$_1$–C$_4$-alkylene bridge, which contains one or two hetero atoms selected from the group consisting of oxygen and nitrogen and is unsubstituted or substituted by methyl, ethyl, propyl or benzyl;

$R^2$ is —C(=NH)NH$_2$ or —CH$_2$-NH$_2$;

$R^3$ is phenyl, benzyl, quinolyl, benzothienyl or naphthyl; and $R^4$ is:

(a) ethyl, propyl, butyl, pentyl or hexyl, each of which is mono- or disubstituted by one or two substituents selected from the group consisting of —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ and —NH—C(=NH)NH$_2$, (b) a 5, 6- or 7-membered, saturated or unsaturated nitrogen-containing heterocyclic group linked directly or via a C$_1$–C$_4$-alkylene bridge or via a C$_1$–C$_3$-alkylene—CO bridge, which optionally contains one or two additional hetero atoms selected from the group consisting of oxygen and nitrogen and which is unsubstituted or substituted by methyl, ethyl, propyl, 3-hydroxypropyl or benzyl;

(c) cyclopentyl or cyclohexyl, each of which is mono- or disubstituted by one or two substituents selected from the group consisting of —NH$_2$, —NHmethyl, —N(methyl)$_2$, —NHethyl, —N(ethyl)$_2$, NH(n-propyl), —N(n-propyl)$_2$, —NH (iso-propyl), —N(iso-propyl)$_2$, —C(=NH)NH$_2$ and —NH—C(=NH)NH$_2$, or (d) benzyl or phenylethyl, each of which is mono- or disubstituted at the phenyl ring by one or two substituents selected from the group consisting of —NH$_2$, —NHmethyl, —N(methyl)$_2$, —NHethyl, —N(ethyl)$_2$, —NH(n-propyl), —N(n-propyl)$_2$, —NH(iso-propyl), —N(iso-propyl)$_2$, —C(=NH)NH$_2$ and —NH—C(=NH)NH$_2$;

or a tautomer or pharmaceutically acceptable salt thereof.

15. A compound of the formula III, according to claim 10, wherein:

$R^1$ is:

(a) methyl, ethyl, (which is unsubstituted or substituted by hydroxy, methoxy, ethoxy, phenoxy or methoxyphenoxy), propyl (which is unsubstituted or substituted by hydroxy, methoxy or ethoxy), butyl or pentyl, (b) benzyl which is unsubstituted or mono- or disubstituted at the phenyl ring by one or two substituents selected from the group consisting of hydroxy, carboxy, methoxycarbonyl, ethoxycarbonyl, methoxy, ethoxy or CF$_3$, or (c) a 5- or 6-membered, saturated or unsaturated heterocyclic group linked directly or via a methylene or ethylene bridge which contains oxygen or nitrogen as the heteroatom and which is unsubstituted or substituted by methyl, ethyl, propyl or benzyl;

$R^2$ is —C(=NH)NH$_2$ or —CH$_2$-NH$_2$;

$R^3$ is phenyl, benzyl, quinolyl, isoquinolyl, benzothienyl or naphthyl; and, $R^4$ is:

(a) ethyl or propyl, each of which is substituted by —NH$_2$, —N(methyl)$_2$, —N(ethyl)$_2$, —N(n-propyl)$_2$ or —C(=NH)NH$_2$, (b) a 5-, 6- or 7-membered, saturated or unsaturated nitrogen-containing heterocyclic group linked directly or via a methylene or ethylene bridge, which optionally contains an oxygen as a further heteroatom and which is unsubstituted or substituted by methyl, ethyl, propyl, 3-hydroxypropyl or benzyl, (c) cyclopentyl or cyclohexyl, each of which is substituted by —NH$_2$, —N(methyl)$_2$, —N(ethyl)$_2$, —N(n-propyl)$_2$ or —C(=NH)NH$_2$, or (d) benzyl which is substituted at the phenyl ring by —NH$_2$, —N(methyl)$_2$, —N(ethyl)$_2$, —N(n-propyl)$_2$ or —C(=NH)NH$_2$, or a tautomer or pharmaceutically acceptable salt thereof.

16. A compound of the formula III, according to claim 10, wherein:

$R^1$ is (a) methyl, ethyl, hydroxyethyl, methoxyethyl, methoxy-phenoxy-ethyl, propyl, hydroxypropyl, ethoxypropyl, or pentyl, or (b) benzyl, which is mono- or disubstituted at the phenyl ring by one or two substituted selected from the group consisting of carboxy, ethoxycarbonyl, or CF$_3$;

$R^2$ is —C(=NH)NH$_2$ or —CH$_2$-NH$_2$;

$R^3$ is phenyl, benzyl, quinolyl, benzothienyl or naphthyl; and, $R^4$ is:

(a) diethylaminoethyl or diethylaminopropyl, (b) a pyridine, pyrimidine, pyrrolidine, morpholine, azepine or piperidine linked directly or via a methylene or methylcarbonyl bridge, each of which is unsubstituted or substituted by methyl, 3-hydroxypropyl or benzyl, or cyclohexyl substituted by —N(n-propyl)$_2$, or (c) benzyl which is substituted at the phenyl ring by —N(methyl)$_2$ or —C(=NH)NH$_2$;

or a tautomer or pharmaceutically acceptable salt thereof.

17. A compound of formula III, according to claim 10, wherein:

$R^1$ methyl, hydroxyethyl, methoxyethyl, methoxyphenoxy-ethyl, propyl, hydroxypropyl, ethoxypropyl, phenylethyl, phenylpropyl or a tetrahydrofuranyl linked via a methylene bridge;

$R^2$ is —C(=NH)NH$_2$ or —CH$_2$-NH$_2$;

$R^3$ is phenyl, benzyl, quinol-8-yl, benzo[b]thien-3-yl or naphthyl; and, $R^4$ is:
 (a) diethylaminoethyl or diethylaminopropyl,
 (b) pyridine linked directly or via a methylene or ethylene bridge, which is unsubstituted or substituted by methyl or benzyl,
 (c) pyrrolidine linked directly or via a methylene or ethylene bridge, which is unsubstituted or substituted by methyl or benzyl,
 (d) piperidine linked directly or via a methylene or ethylene bridge which is unsubstituted or substituted by methyl or benzyl,
 (e) morpholine linked directly or via a methylene or ethylene bridge,
 (f) azepine linked directly or via a methylene or ethylene bridge,
 (g) cyclohexyl substituted by —N(n-propyl)$_2$, or
 (h) benzyl substituted at the phenyl ring by —N(methyl))$_2$;

or a tautomer or pharmaceutically acceptable salt thereof.

* * * * *